US012201685B2

(12) United States Patent
Johnson et al.

(10) Patent No.: US 12,201,685 B2
(45) Date of Patent: *Jan. 21, 2025

(54) METHODS OF MODULATING IMMUNE RESPONSES WITH CATIONIC LIPID VACCINE COMPOSITIONS

(71) Applicants: PDS BIOTECHNOLOGY CORPORATION, North Brunswick, NJ (US); THE GOVERNMENT OF THE USA AS REPRESENTED BY THE SEC OF THE DEPT. OF HEALTH AND HUMAN SERVICES, Rockville, MD (US)

(72) Inventors: Kenya Johnson, Mason, OH (US); Eric Jacobson, Cincinnati, OH (US); Frank Bedu-Addo, Bethel, CT (US); Mikayel Mkrtichyan, Rockville, MD (US); Samir N. Khleif, Silver Spring, MD (US)

(73) Assignees: PDS Biotechnology Corporation, North Brunswick, NJ (US); The United States of America as Represented by the Secretary of the Department of Health and Human Services, Rockville, MD (US)

( * ) Notice: Subject to any disclaimer, the term of this patent is extended or adjusted under 35 U.S.C. 154(b) by 408 days.

This patent is subject to a terminal disclaimer.

(21) Appl. No.: 17/061,464

(22) Filed: Oct. 1, 2020

(65) Prior Publication Data

US 2021/0100898 A1 Apr. 8, 2021

Related U.S. Application Data

(60) Continuation of application No. 16/367,546, filed on Mar. 28, 2019, now Pat. No. 10,828,364, which is a division of application No. 14/407,419, filed as application No. PCT/US2013/045578 on Jun. 13, 2013, now Pat. No. 10,286,064.

(60) Provisional application No. 61/660,172, filed on Jun. 15, 2012.

(51) Int. Cl.
  *A61K 39/39* (2006.01)
  *A61K 39/00* (2006.01)
  *A61K 39/12* (2006.01)

(52) U.S. Cl.
  CPC .......... *A61K 39/39* (2013.01); *A61K 39/0005* (2013.01); *A61K 39/0011* (2013.01); *A61K 39/12* (2013.01); *A61K 2039/55511* (2013.01); *A61K 2039/55516* (2013.01); *A61K 2039/55522* (2013.01); *A61K 2039/55555* (2013.01); *A61K 2039/55566* (2013.01); *A61K 2039/585* (2013.01); *C12N 2710/20034* (2013.01)

(58) Field of Classification Search
  CPC ................................. A61K 39/39; A61K 39/12
  See application file for complete search history.

(56) References Cited

U.S. PATENT DOCUMENTS

| | | |
|---|---|---|
| 2,167,480 A | 7/1939 | Hansell |
| 4,703,004 A | 10/1987 | Hopp et al. |
| 5,264,618 A | 11/1993 | Felgner et al. |
| 5,283,185 A | 2/1994 | Epand et al. |
| 5,334,761 A | 8/1994 | Gebeyehu et al. |
| 5,459,127 A | 10/1995 | Felgner et al. |
| 5,827,703 A | 10/1998 | Debs et al. |
| 6,008,202 A | 12/1999 | Huang et al. |
| 6,124,270 A | 9/2000 | Haensler |
| 6,183,745 B1 | 2/2001 | Tindle et al. |
| 6,214,804 B1 | 4/2001 | Felgner et al. |
| 6,419,931 B1 | 7/2002 | Vitiello et al. |
| 6,464,980 B1 | 10/2002 | Fikes et al. |
| 6,586,409 B1 | 7/2003 | Wheeler |
| 6,610,321 B2 | 8/2003 | Huang et al. |
| 6,649,170 B1 | 11/2003 | Lindblad et al. |
| 6,693,086 B1 | 2/2004 | Dow et al. |
| 6,710,035 B2 | 3/2004 | Felgner et al. |
| 6,780,421 B1 | 8/2004 | Haensler et al. |
| 6,852,334 B1 | 2/2005 | Cullis et al. |
| 7,001,614 B2 | 2/2006 | Smyth-Templeton et al. |
| 7,105,574 B1 | 9/2006 | Wheeler |
| 7,303,881 B2 | 12/2007 | Huang et al. |
| 7,488,791 B2 | 2/2009 | Maillere et al. |
| 8,877,206 B2 | 11/2014 | Chen et al. |
| 9,102,950 B2 | 8/2015 | Hartikka et al. |
| 9,789,129 B2 | 10/2017 | Vasievich et al. |
| 10,155,049 B2 | 12/2018 | Bonnet et al. |

(Continued)

FOREIGN PATENT DOCUMENTS

| | | |
|---|---|---|
| CN | 1909918 A | 2/2007 |
| CN | 101027317 A | 8/2007 |

(Continued)

OTHER PUBLICATIONS

Taiwanese Office Action dated Jun. 20, 2016, from counterpart Taiwanese Application No. 102121266, along with an English Translation of the Search Report.
Supplementary European Search Report dated Jan. 22, 2016, from counterpart European Appln. No. 13804165.2.
Office Action from counterpart Taiwanese Patent Appln. No. 106109798 and its English translation; mail dated Nov. 14, 2017.

(Continued)

Primary Examiner — Elly-Gerald Stoica
(74) Attorney, Agent, or Firm — DLA Piper LLP (US)

(57) ABSTRACT

The present disclosure provides vaccine compositions comprising at least one adjuvant and at least one therapeutic factor. The disclosure also provides methods of reducing an immune suppressor cell population in a mammal, methods of argumenting an immune response in a mammal, and methods of treating a diseases in a mammal utilizing the vaccine compositions.

18 Claims, 4 Drawing Sheets

Specification includes a Sequence Listing.

(56) References Cited

U.S. PATENT DOCUMENTS

| | | |
|---|---|---|
| 10,286,064 B2 | 5/2019 | Johnson et al. |
| 10,702,541 B2 | 7/2020 | Vasievich et al. |
| 10,828,364 B2 | 11/2020 | Johnson et al. |
| 11,401,306 B2 | 8/2022 | Bedu-Addo et al. |
| 11,612,652 B2 | 3/2023 | Bedu-Addo et al. |
| 11,638,753 B2 | 5/2023 | Bedu-Addo et al. |
| 11,738,072 B2 | 8/2023 | Wei et al. |
| 11,801,257 B2 | 10/2023 | Vasievich et al. |
| 11,911,359 B2 | 2/2024 | Chen et al. |
| 2001/0026937 A1 | 10/2001 | Punnonen et al. |
| 2002/0007173 A1 | 1/2002 | Kundig et al. |
| 2002/0187105 A1 | 12/2002 | Zou et al. |
| 2003/0008813 A1 | 1/2003 | Felgner et al. |
| 2003/0228634 A1 | 12/2003 | Simard et al. |
| 2003/0229040 A1 | 12/2003 | Kasid et al. |
| 2004/0106551 A1 | 6/2004 | Khleif et al. |
| 2004/0157791 A1 | 8/2004 | Dow et al. |
| 2004/0170644 A1 | 9/2004 | Mailere et al. |
| 2004/0185057 A1 | 9/2004 | Kirkby et al. |
| 2004/0203051 A1 | 10/2004 | Simard et al. |
| 2005/0025822 A1 | 2/2005 | Wong et al. |
| 2005/0112559 A1 | 5/2005 | Leung et al. |
| 2005/0176672 A1 | 8/2005 | Scheule et al. |
| 2005/0220814 A1 | 10/2005 | Dominowski et al. |
| 2005/0245446 A1 | 11/2005 | Hailes et al. |
| 2006/0008472 A1 | 1/2006 | Huang et al. |
| 2006/0051405 A1 | 3/2006 | MacLachlan et al. |
| 2006/0083780 A1 | 4/2006 | Heyes et al. |
| 2006/0159738 A1 | 7/2006 | Graham et al. |
| 2006/0165708 A1 | 7/2006 | Mayumi et al. |
| 2006/0171956 A1 | 8/2006 | Bareholz et al. |
| 2006/0182793 A1 | 8/2006 | Bachmann et al. |
| 2006/0204566 A1 | 9/2006 | Smyth-Templeton et al. |
| 2006/0223769 A1 | 10/2006 | Dow et al. |
| 2006/0251726 A1 | 11/2006 | Lin et al. |
| 2006/0263804 A1 | 11/2006 | Robinson et al. |
| 2006/0275777 A1 | 12/2006 | Waelti |
| 2006/0286124 A1 | 12/2006 | Burt et al. |
| 2007/0014807 A1 | 1/2007 | Maida, III |
| 2007/0059318 A1 | 3/2007 | Balu-Iyer et al. |
| 2007/0066552 A1 | 3/2007 | Clarke |
| 2007/0207526 A1 | 9/2007 | Coit et al. |
| 2008/0014251 A1 | 1/2008 | Benz et al. |
| 2008/0014254 A1 | 1/2008 | Platscher et al. |
| 2008/0049957 A1 | 2/2008 | Topholm |
| 2008/0131455 A1 | 6/2008 | Huang et al. |
| 2008/0152665 A1 | 6/2008 | Leclerc et al. |
| 2008/0206286 A1 | 8/2008 | Yu |
| 2008/0248044 A1 | 10/2008 | Choppin et al. |
| 2009/0001705 A1 | 1/2009 | Fischer et al. |
| 2009/0017057 A1 | 1/2009 | Chen et al. |
| 2009/0053251 A1 | 2/2009 | Pogue-Caley et al. |
| 2010/0086584 A1 | 4/2010 | Callejo et al. |
| 2010/0099745 A1 | 4/2010 | Sambhara et al. |
| 2010/0112002 A1 | 5/2010 | Lien et al. |
| 2010/0158939 A1 | 6/2010 | Sambhara et al. |
| 2010/0189742 A1 | 7/2010 | Van Der Burg et al. |
| 2010/0203080 A1 | 8/2010 | Maillere et al. |
| 2010/0221223 A1 | 9/2010 | Tsutsui et al. |
| 2010/0239657 A1 | 9/2010 | Kim et al. |
| 2010/0266547 A1 | 10/2010 | Benedict |
| 2010/0297144 A1 | 11/2010 | Roden |
| 2011/0110972 A1 | 5/2011 | Vasievich |
| 2011/0117141 A1 | 5/2011 | Huang et al. |
| 2011/0158952 A1 | 6/2011 | Beach et al. |
| 2011/0305713 A1 | 12/2011 | Munn et al. |
| 2012/0064035 A1 | 3/2012 | Hadden et al. |
| 2012/0148622 A1 | 6/2012 | tenOever |
| 2013/0129761 A1 | 5/2013 | Garcia-Sastre et al. |
| 2013/0225663 A1 | 8/2013 | Brown |
| 2013/0243723 A1 | 9/2013 | Hadden et al. |
| 2015/0079155 A1 | 3/2015 | Jensen et al. |
| 2015/0093410 A1 | 4/2015 | Chen et al. |
| 2015/0110823 A1 | 4/2015 | Bedu-Addo et al. |
| 2015/0132340 A1 | 5/2015 | Kenya et al. |
| 2015/0250872 A1 | 9/2015 | Bedu-Addo et al. |
| 2015/0283219 A1 | 10/2015 | Langlade Demoyen et al. |
| 2015/0343062 A1 | 12/2015 | Kuboyama et al. |
| 2016/0168227 A1 | 6/2016 | Kallen et al. |
| 2016/0193316 A1 | 7/2016 | Sette et al. |
| 2016/0251406 A1 | 9/2016 | Schlom et al. |
| 2017/0296639 A1 | 10/2017 | Ma et al. |
| 2018/0015114 A1 | 1/2018 | Vasievich et al. |
| 2018/0094032 A1 | 4/2018 | Bedu-Addo et al. |
| 2018/0221475 A1 | 8/2018 | Bedu-Addo et al. |
| 2018/0353599 A1 | 12/2018 | Bedu-Addo et al. |
| 2019/0321321 A1 | 10/2019 | Bedu-Addo et al. |
| 2019/0358319 A1 | 11/2019 | Bedu-Addo et al. |
| 2020/0121770 A1 | 4/2020 | Wei et al. |

FOREIGN PATENT DOCUMENTS

| | | |
|---|---|---|
| CN | 101065350 A | 10/2007 |
| CN | 101193655 A | 6/2008 |
| CN | 101702882 A | 5/2010 |
| CN | 102137675 A | 7/2011 |
| CN | 104189897 A | 12/2014 |
| CN | 104703588 A | 6/2015 |
| CN | 105101991 A | 11/2015 |
| CN | 105163753 A | 12/2015 |
| CN | 105920599 A | 9/2016 |
| CN | 111217918 A | 6/2020 |
| EP | 2167480 A2 | 3/2010 |
| JP | H06510051 A | 11/1994 |
| JP | H09502086 A | 3/1997 |
| JP | H10501822 A | 2/1998 |
| JP | 2002537102 A | 11/2002 |
| JP | 2002542341 A | 12/2002 |
| JP | 2003506095 A | 2/2003 |
| JP | 2003509035 A | 3/2003 |
| JP | 2004508012 A | 3/2004 |
| JP | 2006513979 A | 4/2006 |
| JP | 2006527762 A | 12/2006 |
| JP | 2007238559 A | 9/2007 |
| JP | 2008521757 A | 6/2008 |
| JP | 2010522206 A | 7/2010 |
| JP | 2010537961 A | 12/2010 |
| JP | 2011518170 A | 6/2011 |
| JP | 2012526853 A | 11/2012 |
| JP | 2014527965 A | 10/2014 |
| JP | 2015521601 A | 7/2015 |
| JP | 2015530413 A | 10/2015 |
| KR | 20150058139 A | 5/2015 |
| RU | 2311911 C2 | 12/2007 |
| TW | 200902060 A | 1/2009 |
| TW | 201000124 A | 1/2010 |
| TW | I589298 | 4/2014 |
| WO | WO-9303709 A1 | 3/1993 |
| WO | WO-9303764 A1 | 3/1993 |
| WO | 93/22338 | 11/1993 |
| WO | WO-9504542 A1 | 2/1995 |
| WO | WO-9527508 A1 | 10/1995 |
| WO | WO-9703703 A1 | 2/1997 |
| WO | WO-0050006 A2 | 8/2000 |
| WO | WO-0062813 A2 | 10/2000 |
| WO | 00/77043 A2 | 12/2000 |
| WO | WO-0111067 A1 | 2/2001 |
| WO | WO-0119408 A1 | 3/2001 |
| WO | WO-0157068 A1 | 8/2001 |
| WO | WO-0180900 A2 | 11/2001 |
| WO | WO-02069369 A2 | 9/2002 |
| WO | WO-02097116 A2 | 12/2002 |
| WO | WO-03000398 A2 | 1/2003 |
| WO | WO-03003985 A2 | 1/2003 |
| WO | WO-03011252 A1 | 2/2003 |
| WO | WO-03095641 A1 | 11/2003 |
| WO | WO-2004014957 A1 | 2/2004 |
| WO | WO 2004089413 A1 | 10/2004 |
| WO | WO 2005000889 A1 | 1/2005 |
| WO | 2006/063382 | 6/2006 |
| WO | WO-2007022152 A2 | 2/2007 |
| WO | WO-2007121895 A2 | 11/2007 |
| WO | WO-2008116078 A2 | 9/2008 |
| WO | 2008/148057 A2 | 12/2008 |

(56) References Cited

FOREIGN PATENT DOCUMENTS

| WO | 2009/129227 | 10/2009 |
|---|---|---|
| WO | WO-2008116078 A4 | 10/2009 |
| WO | WO-2009142892 A1 | 11/2009 |
| WO | 2010/101663 | 9/2010 |
| WO | WO-2011083820 A1 | 7/2011 |
| WO | WO-2013016675 A1 | 1/2013 |
| WO | WO-2013188627 A2 | 12/2013 |
| WO | WO-2014047533 A1 | 3/2014 |
| WO | WO-2015061416 A2 | 4/2015 |
| WO | WO-2015176662 A1 | 11/2015 |
| WO | WO-2016146618 A1 | 9/2016 |
| WO | WO-2017083820 A1 | 5/2017 |

OTHER PUBLICATIONS

Dranoff G., GM-CSF based vaccines, Immunol. Rev. 188, 147-154, 2002.
Office Action for counterpart Russian Application No. 2015101110 along with its English translation; mail dated Aug. 8, 2017.
Office Action for counterpart Russian Application No. 2015101110 along with its English translation; mail dated Mar. 28, 2017.
Sinha et al. (2007) Cross-Talk between Myeloid-Derived Suppressor Cells and Macrophages Subverts Tumor Immunity toward a Type 2 Response, J. Immunol. 179:977-983.
Gabrilovich et al. (2009) Myeloid-derived-suppressor cells as regulators of the immune system. Nat. Rev. Immunol. 9(3): 162-174 (pp. 1-26 NIH Manuscript).
First Examination Report from counterpart Indian Appln. No. 11144/DELNP/2014 dated Mar. 7, 2019.
Perales et al., "Phase I/II study of GM-CSF DNA as an adjuvant for a multipeptide cancer vaccine in patients with advanced melanoma", Molecular Therapy, vol. 16, 2008, pp. 2022-2029.
Vasievich et al., "Trp2 peptide vaccine adjuvanted with ®-DOTAP inhibits tumor growth in an advanced melanoma model", Mol. Pharmaceutics, vol. 9, 2012, pp. 261-268.
Extended European Search Report from counterpart European Application No. 19203293.6 dated Mar. 10, 2020.
Berraondo, Pedro et al., "Eradication of large tumors in mice by a tritherapy targeting the innate, adaptive, and regulatory components of the immune system", Cancer Research, 2007, vol. 67, No. 17, pp. 8847-8855.
Vangasseri, Dileep P. et al., "Immunostimulation of dendritic cells by cationic liposomes", Molecular Membrane Biology, 2006, vol. 23, No. 5, pp. 385-395.
"3,5,9-Trioxa-4-phosphaheptacos-18-en-1-aminium, 4-ethoxy-N, N, N-trimethyl-10-oxo-7-[[(9Z)-1-oxo-9-octadecen-1-yl]oxy]-, 4-oxide, (7R, 18Z)-," Registry, Chemical Abstracts Service, Columbus, Ohio, US, Database Accession No. 183283-20-7, Nov. 22, 1996, 02 pages, XP002694550.
Alving C.R., "Design And Selection Of Vaccine Adjuvants: Animal Models And Human Trials," Vaccine, Elsevier Science Ltd, 2002, vol. 20, pp. S56-S64.
Anderson P., "Effective Vaccination of Mice Against Mycobacterium Tuberculosis Infection With A Soluble Mixture of Secreted Mycobacterial Proteins," Infection and Immunity, American Society for Microbiology, Jun. 1994, vol. 62, No. 6, pp. 2536-2544.
Aramaki Y., et al., "Induction of Apoptosis in WEHI 231 Cells by Cationic Liposomes," Pharmaceutical Research, Plenum Publishing Corporation, Jan. 18, 2000, vol. 17, No. 5, pp. 515-520.
Baecher-Allan C., et al., "Immune Regulation In Tumor-Bearing Hosts," Current Opinion In Immunology, Elsevier Limited, 2006, vol. 18, pp. 214-219.
Baecher-Allan C., et al., "Suppressor T Cells in Human Diseases," Journal of Experimental Medicine, The Rockefeller University Press, Aug. 2, 2004, vol. 200, No. 3, pp. 273-276.
Banchereau J., et al., "Dendritic Cells And The Control of Immunity," Nature, Mar. 19, 1998, vol. 392, No. 6673, pp. 245-252.
Bei R., et al., "The Use of a Cationic Liposome Formulation (DOTAP) Mixed with a Recombinant Tumor-Associated Antigen to Induce Immune Responses and Protective Immunity in Mice," Journal of Immunotherapy, 1998, vol. 21, No. 3, 2 Pages, Abstract only.
Bei R., et al., "The Use of a Cationic Liposome Formulation (DOTAP) Mixed With a Recombinant Tumor-associated Antigen to Induce Immune Responses and Protective Immunity in Mice," Journal Of Immunotherapy, Lippincott Williams & Wilkins, Hagerstown, MD, US, Jan. 1, 1998, vol. 21, No. 3, pp. 159-169, ISSN 1524-9557, XP002963675.
Benmohamed L., et al., Lipopeptide Immunization Without Adjuvant Induces Potent And Long-Lasting B, T Helper, And Cytotoxic T Lymphocyte Resonses Against A Malaria Liver Stage Antigen In Mice And Chimpanzees, European Journal Of Immunology, VCH Verlagsgesellschaft, 1997, vol. 27, pp. 1242-1253.
Black M., et al., "Advances In The Design And Delivery Of Peptide Subunit Vaccines With A Focus On Toll-like Receptor Agonists." Expert Rev. Vaccines, vol. 9, No. 2, 2010, pp. 157-173.
Brunel F., et al., "Cationic Lipid DC-Chol Induces an Improved and Balanced Immunity Able to Overcome the Unresponsiveness to the Hepatitis B Vaccine," Vaccine, Apr. 1999, vol. 17, pp. 2192-2203.
Brunette E., et al., "Lipofection Does Not Require the Removal of Serum," Nucleic Acids Research, Cancer Research Institute, University Of California San Francisco Medical Center, San Francisco, California, Dec. 26, 1991, vol. 20, No. 5, p. 1151.
Byers A.M., et al., "Cutting Edge: Rapid In Vivo CTL Activity by Polyoma Virus-Specific Effector and Memory CD8+ T Cells," The American Association of Immunologists Inc., The Journal of Immunology, 2003, vol. 171, pp. 17-21.
Cantor H., et al., "Immunoregulatory Circuits Among T-Cell Sets II. Physiologic Role of Feedback Inhibition in Vivo: Absence in NZB Mice," The Rockefeller University Press, Journal of Experimental Medicine, 1978, pp. 1116-1125.
Carr M.W., et al., "Monocyte Chemoattractant Protein 1 Acts As AT-Lymphocyte Chemoattractant," Proceedings Of The National Academy Of Sciences of The United States Of America, Committee On Immunology and Department Of Pathology, Harvard Medical School, Department Of Cardiology, Childen's Hospital, and The Center For Blood Research, Boston, Massachusetts, Apr. 1994, vol. 91, pp. 3652-3656.
Castellino F., et al., "Chemokine-Guided CD4+ T Cell Help Enhances Generation Of IL-6Ra high IL-7Ra high Prememory COB+ T Cells," The Journal Of Immunology, Lymphocyte Biology Section, Laboratory Of Immunology, National Institute Of Allergy And Infectious Diseases, National Institutes Of Health, Bethesda, Maryland, 2007, vol. 178, pp. 778-787.
Castellino F., et al., "Chemokines Enhance Immunity By Guiding Naive COB+ T Cells To Sites Of CD4+ T Cell-Dendritic Cell Interaction," Nature, Lymphocyte Biology Section, Laboratory Of Immunology, National Institute Of Allergy And Infectious Diseases, National Institutes Of Health, Bethesda, Maryland, Apr. 13, 2006, vol. 440, pp. 890-895.
Chen W., et al., "A Simple and Effective Cancer Vaccine Consisting of an Antigen and a Cationic Lipid," Division of Molecular Pharmaceutics, School of Pharmacy, University of North Carolina, Chapel Hill, Chapel Hill, North Carolina, USA, 2008, pp. 1-48.
Chen W., et al., "A Simple But Effective Cancer Vaccine Consisting Of An Antigen And A Cationic Lipid," Cancer Immunology, Immunotherapy, Springer, Berlin, DE, Aug. 28, 2007, vol. 57, No. 4, pp. 517-530, ISSN 1432-0851, XP019586704.
Chen W., et al., "Induction of Cytotoxic T-Lymphocytes and Antitumor Activity by a Liposomal Lipopeptide Vaccine," Molecular Pharmaceutics, 2008, vol. 5, No. 3, pp. 464-471.
Chen W.C., et al., "Cationic Liposome-Based Peptide Vaccine: Potent Therapeutics for Cervical Cancer," Poster, School of Pharmacy, May 20, 2006, 1 Page.
Chikh G., et al., "Liposomal Delivery of CTL Epitopes to Dendritic Cells, Bioscience Reports," Plenum Publishing Corporation, Apr. 2002, vol. 22, No. 2, pp. 339-353.
Christensen D., et al., "Cationic Liposomes as Vaccine Adjuvants," Expert Review of Vaccines, Oct. 2007, vol. 6, No. 5, pp. 785-796, XP008137314.
Cohen P.A., et al., "CD4+ T-Cells From Mice Immunized To Syngeneic Sarcomas Recognize Distinct, Non-Shared Tumor Anti-

(56) References Cited

OTHER PUBLICATIONS gens," Cancer Research, Branches Of Surgery And Dermatology, National Cancer Institute, National Institute Of Health, Bethesda, Maryland, Feb. 15, 1994, vol. 54, pp. 1055-1058.

Comes A., et al., "CD25+ Regulatory T Cell Depletion Augments Immunotherapy of MicroMetastases by an IL-21-Secreting Cellular Vaccine1," The Journal of Immunology, The American Association of Immunologists Incorporated, 2006, pp. 1750-1758.

Communication about Intention to Grant a European Patent received for European Application No. 08799629.4, mailed on Jun. 1, 2015, 6 Pages.

Communication about Intention to Grant a European Patent Received for European Application No. 09733034.4, mailed on Jul. 6, 2018, 6 Pages.

Communication about Intention to Grant a European Patent Received for European Application No. 12831495.2, mailed on Feb. 16, 2018, 10 Pages.

Communication about Intention to Grant a European Patent Received for European Application No. 13804165.2, mailed on May 9, 2019, 7 Pages.

Connor J., et al., "pH-Sensitive Immunoliposomes as an Efficient and Target-Specific Carrier for Antitumor Drugs," Cancer Research, Department of Biochemistry, University of Tennessee, KnoxvilleTennessee, Jul. 1986, vol. 46, pp. 3431-3435.

Copland M.J., et al., "Lipid Based Particulate Formulations for the Delivery of Antigen," Immunology and Cell Biology, Australasian Society for Immunology Incorporate, 2005, vol. 83, pp. 97-105. Credo Reference, 2005.

Cui Z., et al., "Coating of Mannan on LPD Particles Containing HPV E7 Peptide Significantly Enhances Immunity Against HPV-Positive Tumor," Pharmaceutical Research, Jun. 2004, vol. 21, No. 6, pp. 1018-1025.

Cui Z., et al., "Immunostimulation Mechanism of LPD Nanoparticle as a Vaccine Carrier," Molecular Pharmaceutics, American Chemical Society, 2005, vol. 2, No. 1, pp. 22-28.

Cui Z., et al., "Liposome-Polycation-DNA (LPD) Particle As A Carrier and Adjuvant for Protein-Based Vaccines: Therapeutic Effect Against Cervical Cancer," Cancer Immunology and Immunother, Springer-Verlag, 2005, vol. 54, pp. 1180-1190.

Datta G., et al., "Effects of Increasing Hydrophobicity on the Physical-Chemical and Biological Properties of a Class A Amphipathic Helical Peptide," Journal of Lioid Research, 2001, vol. 42, pp. 1096-1104.

Davies G., "Adjuvant Activity of Cytokines," Chapter 19, Methods in Molecular Biology, 2010, ISSN: 0003658713, pp. 287-309.

De Bruijn M.L.H., et al., "Immunization With Human Papillomavirus Type 16 (Hpv16) Oncoproteinoloaded Dendritic Cells As Well As Proteinin Adjuvant Induces Mhc Class 1-restricted Protection To Hpv16-induced Tumor Cells," Cancer Research, Feb. 15, 1998, vol. 58, No. 4, pp. 724-731.

Decision of Rejection from Corresponding Japanese Patent Application No. JP2018524752, dated Jul. 13, 2021, 6 Pages.

Decision on the Request for Reexamination from Corresponding Chinese Application No. 200880017151.0, dated Jun. 12, 2017, 18 pages.

Decision to Grant a European Patent received for European Application No. 08799629.4, mailed on Oct. 15, 2015, 3 Pages.

Decision to Grant a European Patent received for European Application No. 09733034.4, mailed on Oct. 25, 2018, 2 Pages.

Decision to Grant a European Patent Received for European Application No. 12831495.2, mailed on Jun. 7, 2018, 2 Pages.

Decision to Grant a European Patent received for European Application No. 13804165.2, mailed on Sep. 19, 2019, 3 Pages.

Decker T., et al., "The Yin and Yang of Type I Interferon Activity in Bacterial Infection," Nature Reviews Immunology, 2005, vol. 5, pp. 675-687.

Denning D.W., et al., "Micafungin (FK463), Alone or in Combination with Other Systemic Antifungal Agents, for the Treatment of Acute Invasive Aspergillosis," Journal Of Infection, Elsevier Ltd, 2006, vol. 53, pp. 337-349.

Desilva D.R, et al., "The p38 Mitogen-Activated Protein Kinase Pathway in Activated and Anergic Th1 Cells," Cellular Immunology, Academic Press, 1997, vol. 180, pp. 116-123.

Diamond D.J., et al., "Development of a Candidate HLA A 0201 Restricted Peptide-Based Vaccine Against Human Cytomegalovirus Infection," Blood, Sep. 1, 1997, vol. 90, No. 05, pp. 1751-1767.

Dileo J., et al., "Lipid-Protamine-DNA-Mediated Antigen Delivery to Antigen-Presenting Cells Results in Enhanced Anti-Tumor Immune Responses," The American Society of Gene Therapy, Molecular Therapy, May 2003, vol. 7, No. 5, pp. 640-648.

Dillon S., et al., "A Toll-Like Receptor 2 Ligand Stimulates Th2 Responses In Vivo, Via Induction Of Extracellular Signal-Regulated Kinase Mitogen-Activated Protein Kinase and c-Fos In Dendritic Cells," The Journal Of Immunology, The American Association Of Immunologists, Inc., 2004, vol. 172, 12 Pages.

Dolcetti L., et al., "Hierarchy of Immunosuppressive Strength Among Myeloid-derived Suppressor Cell Subsets is determined by GM-CSF," European Journal of Immunology, 2010, vol. 40, pp. 22-35.

Dong C., et al., "MAP Kinases in the Immune Response," Annual Review of Immunology, Annual Reviews, 2002, vol. 20, pp. 55-72.

Dow S.W., et al., "Lipid-DNA Complexes Induce Potent Activation of Innate Immune Responses and Antitumor Activity When Administered Intravenously," The Journal of Immunology, 1999, vol. 163, pp. 1552-1561.

Dupuis M., et al., "Dendritic Cells Internalize Vaccine Adjuvant After Intramuscular Injection," Cellular Immunology, Academic Press, 1998, vol. 186, pp. 18-27.

Eardley D.D., et al., "Immunoregulatory Circuits Among T-Cell Sets I. T-Helper Cells Induce Other T-Cell Sets to Exert Feedback Inhibition," The Rockefeller University Press, Journal of Experimental Medicine, 1978, pp. 1106-1115.

EMBL Database Entry GG774706, Bacteroides sp. 1_ 1_ 14 Genomic Scaffold Supercont1.5, Jun. 15, 2010, 202 Pages, [Retrieved on Oct. 28, 2013), Retrieved from the Internet: http://www.ebi.ac.uk/ena/data/view/GG774706&display=text.

English Translation of Chinese First Office Action of Corresponding Chinese Application No. 201380060902.8, dated May 26, 2016, 12 Pages.

English Translation of First Office Action from Corresponding Chinese Application No. 201710819740.1, dated Jul. 17, 2020, 21 Pages.

English Translation of First Office Action in Counterpart Chinese Application No. 201880088575.X, dated Dec. 29, 2021, 21 Pages.

English Translation of Fist Office Action from Corresponding Chinese Patent Application No. 201710819740.1, dated Apr. 29, 2021, 15 Pages.

English Translation of Notice of Reasons for Refusal Received in Corresponding Japanese Patent Application No. 2018-524752 dated Sep. 3, 2020, 8 Pages.

English Translation of Notification of Defects from Corresponding Israel Application No. 259294, dated May 5, 2021, 6 Pages.

English translation of Notification of Reasons for Rejection from Corresponding Japanese Application No. 2014-17712, mailed Sep. 15, 2015, 11 Pages.

English Translation of Office Action from Corresponding Taiwan Application No. 102134251, dated Apr. 24, 2017, 13 Pages.

English Translation of Office Action in Taiwanese Application No. 101133392, mailed Nov. 2, 2015, 16 pages.

English Translation of Office Action Japanese Application No. JP2014529976, mailed Jul. 11, 2017, 07 pages.

English Translation of Third Chinese Office Action from Corresponding Chinese Application No. 201380060902.8, dated Oct. 18, 2017, 27 Pages.

English Translation of Third Office Action from Corresponding Chinese Application No. 200980121761.X, dated May 9, 2016, 10 Pages.

European Communication Corresponding European Application No. EP12831495.2 dated Jun. 6, 2016, 5 pages.

European Search Report and Written Opinion prepared for EP12831495 completed on Mar. 5, 2015, 8 Pages.

Examination Report No. 1 for Corresponding Australian Application No. 2013317805, mailed Jul. 11, 2017, 4 Pages.

(56) References Cited

OTHER PUBLICATIONS

Examination Report No. 2 from Corresponding Australian Patent Application No. 2017340407, dated Jan. 6, 2021, 5 Pages.
Extended European Search Report for European Application No. 13804165.2, mailed Jan. 5, 2016, 5 Pages.
Extended European Search Report for European Application No. 13839199.0, mailed Apr. 4, 2016, 7 Pages.
Extended European Search Report for European Application No. 16865201.4, mailed Jun. 6, 2019, 10 Pages.
Extended European Search Report for European Application No. 17859111.1, mailed May 26, 2020, 7 Pages.
Extended European Search Report for European Application No. 18886648.7, mailed Aug. 11, 2021, 9 Pages.
Extended European Search Report for European Application No. 08799629.4, mailed Mar. 5, 2010, 04 Pages.
Extended European Search Report for European Application No. 09733034.4, mailed Apr. 15, 2013, 07 Pages.
Extended European Search Report for European Application No. 12831495.2, mailed Mar. 16, 2015, 09 Pages.
Felnerova D., et al., "Liposomes and Virosomes as Delivery Systems for Antigens," Nucleic Acids and Drugs, Current Opinion in Biotechnology, Elsevier Ltd, 2004, vol. 15, pp. 518-529.
Feltkamp M.C., et al., "Vaccination with Cytotoxic T Lymphocyte Epitope-containing Peptide Protects Against a Tumor Induced by Human Papillomavirus Type 16-transformed Cells," European Journal Of Immunology, PubMed, Sep. 1993, vol. 23, No. 9, pp. 2242-2249.
Fernandes I., et al., "Synthetic Lipopeptides Incorporated In Liposomes: In Vitro Stimulation OfThe Profliferation Of Murine Splenocytes And In Vivo Induction Of An Immune Response Against A Peptide Antigen," Molecular Immunology, Elsevier Limited, 1997, vol. 34, No. 8/9, pp. 569-576.
Filion M.C., et al., "Anti-Inflammatory Activity of Cationic Lipids," British Journal Of Pharmacology, Oct. 1997, vol. 122, No. 3, pp. 551-557, ISSN 0007-1188, XP002569679.
Filion M.C., "Major Limitations in the Use of Cationic Liposomes for DNA Delivery," International Journal of Pharmaceutics, 1998, vol. 162, No. 1-2, pp. 159-170.
Final Office Action from Corresponding U.S. Appl. No. 15/775,680, dated Jan. 22, 2021, 9 Pages.
First Examination Report from Corresponding Indian Patent Application No. 201618020440, dated Nov. 10, 2020, 4 Pages.
First Office Action from Corresponding Chinese Patent Application No. 201811312211.3, dated Aug. 3, 2021, 27 Pages.
Fuertes M.B., et al., "Host Type I IFN Signals are Required for Antitumor CD8+ T Cell Responses Through CD8α+ Dendritic Cells," Journal of Experimental Medicine, 2011, vol. 208, pp. 2005-2016.
Gahery-Segard H., et al., "Multiepitopic B- And T-Cell Responses Induced in Humans by a Human Immunodeficiency Virus Type 1 Lipopeptide Vaccine," American Society For Microbiology, Journal Of Virology, Feb. 2000, vol. 74, No. 4, pp. 1694-1703.
Gandhapudi S.K., et al., "Antigen Priming With Enantiospecific Cationic Lipid Nanoparticles Induces Potent Antitumor CTL Responses Through Novel Induction Of A Type I IFN Response," Journal of Immunology, May 3, 2019, vol. 202, pp. 3524-3536, Retrieved from URL: http://www.jimmunol.org/contenU202/12/3524.
Glick D., "Methods of Biochemical Analysis," Cancer Biology Research Laboratory, Stanford University Medical Center, Stanford, California, 1988, vol. 33, pp. 337-462.
Gluck R., et al., "Biophysical Validation of Epaxal Berna, a Hepatitis A Vaccine Adjuvanted with Immunopotentiating Reconstituted Influenza Virosomes (IRIV),"Developments in Biologicals, 2000, vol. 103, 12 Pages.
Gold J.S., et al. "A Single Heteroclitic Epitope Determines Cancer Immunity After Xenogeneic Dna Immunization Against A Tumor Differentiation Antigen," The Journal of Immunology, 2003, 170. 10, pp. 5188-5194.
Grabowska et al., "Identification of Promiscuous Hpv16-Derived T Helper Cell Epitopes for Therapeutic Hpv Vaccine Design," International Journal of Cancer, 2015, vol. 136, No. 1, pp. 212-224, XP055497833.
Greenfield I., et al., "Human Papillomavirus 16 E7 Protein is Associated with the Nuclear Matrix," Proceedings of the National Academy of Sciences of the United States of America, Dec. 1991, vol. 88, pp. 11217-11221.
Gregoriadis G., et al., "Vaccine Entrapment in Liposomes," Methods, 1999, vol. 19, pp. 156-162.
Gregoriadis G., "Immunological Adjuvants: A Role for Liposomes," Immunology Today, The School of Pharmacy, University of London, 1990, vol. 11, No. 3, pp. 89-97.
Hamley I.W., "Self-Assembly of Amphiphilic Peptides," Soft Matter, 2011, vol. 7, pp. 4122-4138.
Hartikka J., et al., "Vaxfectin (Registered), A Cationic Lipid-based Adjuvant For Protein-based Influenza Vaccines," 2009, Vaccine, vol. 27, pp. 6399-6403.
Hasegawa A., et al., "Nasal Immunization With Diphtheria Toxoid Conjugated-CD52 Core Peptide Induced Specific Antibody Production In Genital Tract Of Female Mice," American Journal Of Reproductive Immunology, 2002, vol. 48, pp. 305-311.
Hassan C., et al., "Naturally Processed Non-Canonical HLA-A 02:01 Presented Peptides," The Journal of Biological Chemistry, 2015, vol. 290, No. 5, pp. 2593-2603, XP055497822.
Helmby H., et al., "Interleukin-1 Plays A Major Role In The Development OfTh2-Mediated Immunity," European Journal Of Immunology, WHILEY-VCH Verlag GmbH & Co., 2004, vol. 34, pp. 3674-3681.
Holten-Anderson L., et al., "Combination of the Cationic Surfactant Dimethyl Dioctadecyl Ammonium Bromide and Synthetic Mycobacterial Cord Factor as an Efficient Adjuvant for Tuberculosis Subunit Vaccines," Infection and Immunity, Mar. 2004, vol. 72, No. 3, pp. 1608-1617.
Hultner L., "In Activated Mast Cells, IL-1 Up-Regulates The Production Of Several Th2-Related Cytokines Including IL-9," The American Association Of Immunologists, The Journal Of Immunology, 2000, vol. 164, pp. 5556-5563.
Immordino et al., "Stealth Liposomes: Review of the Basic Science, Rationale, and Clinical Applications, Existing and Potential," International Journal of Nanomedicine, 2006, vol. 1, No. 03, pp. 297-315.
Inaba K., et al., "Generation Of Large Numbers Of Dendritic Cells From Mouse Bone Marrow Cultures Supplemented With Granulocyte/Macrophage Colony-Stimulating Factor," Journal Of Experimental Medicine, The Rockefeller University Press, Dec. 1992, vol. 176, pp. 1693-1702.
International Preliminary Report on Patentability for International Application No. PCT/US2009/040500, mailed Oct. 28, 2010, 6 Pages.
International Preliminary Report on Patentability for International Application No. PCT/US2013/045578, mailed Dec. 24, 2014, 7 Pages.
International Preliminary Report on Patentability for International Application No. PCT/US2013/061132, mailed Apr. 2, 2015, 10 Pages.
International Preliminary Report on Patentability for International Application No. PCT/US2017/055119, mailed Apr. 18, 2019, 16 Pages.
International Search Report and Written Opinion for International Application No. PCT/US2009/040500, mailed Jun. 4, 2009, 7 Pages.
International Search Report and Written Opinion for International Application No. PCT/US2013/045578, mailed Nov. 25, 2013, 9 Pages.
International Search Report and Written Opinion for International Application No. PCT/US2013/061132, mailed Dec. 30, 2013, 12 Pages.
International Search Report and Written Opinion for International Application No. PCT/US2017/055119, mailed Mar. 7, 2018, 23 Pages.

(56) References Cited

OTHER PUBLICATIONS

International Search Report and Written Opinion for International Application No. PCT/US2021/060337, mailed Feb. 14, 2022, 7 Pages.

International Preliminary Report on Patentability for International Application No. PCT/US2008/057678, mailed Sep. 22, 2009, 5 Pages.

International Preliminary Report on Patentability for International Application No. PCT/US2012/054786, mailed Mar. 20, 2014, 6 Pages.

International Preliminary Report on Patentability for International Application No. PCT/US2016/061829, mailed May 24, 2018, 15 Pages.

International Preliminary Report on Patentability for International Application No. PCT/US2017/055348, mailed Apr. 18, 2019, 6 Pages.

International Preliminary Report on Patentability for International Application No. PCT/US2018/064060, mailed Jun. 18, 2020, 7 Pages.

International Search Report and Written Opinion for International Application No. PCT/US2008/057678, mailed Apr. 20, 2009, 6 Pages.

International Search Report and Written Opinion for International Application No. PCT/US2012/054786, mailed Nov. 15, 2012, 8 Pages.

International Search Report and Written Opinion for International Application No. PCT/US2016/061829, mailed Feb. 24, 2017, 18 Pages.

International Search Report and Written Opinion for International Application No. PCT/US2017/055348, mailed Jan. 5, 2018, 8 Pages.

International Search Report and Written Opinion for International Application No. PCT/US2018/064060, mailed Apr. 30, 2019, 9 Pages.

International Search Report for International Application No. PCT/US2008/057678, mailed Apr. 20, 2009, 3 Pages.

International Search Report for International Application No. PCT/US2009/040500, mailed Jun. 4, 2009, 2 Pages.

Ishida T., et al., "Defective Function Of Langerhans Cells In Tumor-Bearing Animals is the Result of Defective Maturation from Hemopoietic Progenitors," The American Association Of Immunologists, The Journal Of Immunology, 1998, vol. 161, pp. 4842-4851.

Iwaoka S., et al., "Cationic Liposomes Induce Apoptosis Through p38 MAP-kinase-caspase-8-Bid Pathway in Macrophage-like RAW 264.7 Cells", Journal of Leukocyte Biology, Jan. 2006, vol. 79, pp. 184-191, XP008117765.

Jacob A., et al., "Convergence of Signaling Pathways on the Activation of ERK in B Cells," The Journal of Biological Chemistry, The American Society for Biochemistry and Molecular Biology Incorporated, Jun. 28, 2002, vol. 277, No. 26, pp. 23420-23426.

Jiao X., et al., "Modulation of Cellular Immune Response Against Hepatitis C Virus Nonstructural Protein 3 by Cationic Liposome Encapsulated DNA Immunization," Hepatology, Feb. 2003, vol. 37, No. 2, pp. 452-460.

Jisho: "Kojien," Japanese Dictionary, Third Edition, Iwanami Shoten, 1983, 1 Page.

Johnson G.L., et al., "Mitogen-activated Protein Kinase Pathways Mediated by ERK, JNK, and p38 Protein Kinases," Science, Dec. 6, 2002, vol. 298, pp. 1911-1912.

Jones C.A., et al., "Vaccination Strategies to Prevent Genital Herpes and Neonatal Herpes Simplex Virus (HSV) Disease," Herpes, 2004, vol. 11, pp. 12-17.

Joseph A., et al., "A New Intranasal Influenza Vaccine Based on a Novel Polycationic Lipid-Ceramide Carbamoyl-Spermine (CCS) I. Immunogenicity and Efficacy Studies in Mice," Vaccine, 2006, vol. 24, pp. 3990-4006.

Kabarowski J.H.S., et al., "Lysophospatidylcholine As A Ligand For The Immunoregulatory Receptor G2A," Science, Department Of Microbiology, Immunology, And Molecular Genetics, Department Of Cancer Biology, Lerner Research Institute, Cleveland, Ohio, Jul. 27, 2001, vol. 293, 06 pages.

Kahn J.O., et al., "Clinical and Immunologic Responses to Human Immunodeficiency Virus (HIV) Type 1SF2 GP120 Subunit Vaccine Combined with MF59 Adjuvant with or without Muramyl Tripeptide Dipalmitoyl Phosphatidylethanolamine in Non-HIV-Infected Human Volunteers," The Journal of Infectious Diseases, 1994, vol. 170, pp. 1288-1291.

Kanafani Z.A., et al., "Daptomycin: A Rapidly Bactericidal Lipopeptide for the Treatment of Gram-Positive Infections," Experimental Review of Antibacterial Infections, Future Drugs Ltd, 2007, vol. 5, No. 2, pp. 177-184.

Kantengwa S., et al., "Superoxide Anions Induce The Maturation of Human Dendritic Cells," American Journal of Respiratory and Critical Care Medicine, Divisions of Pneumology and Thoracic Surgery, University Hospital, Geneva, Switzerland, Feb. 1, 2003, vol. 167, No. 3, pp. 431-437.

Kenter G.G., et al., "Vaccination Against Hpv-16 Oncoproteins for Vulvar Intraepithelial Neoplasia," The New England Journal of Medicine, Nov. 5, 2009, vol. 361, pp. 1838-1847.

Kim J.J., et al., "CD8 Positive T Cells Influence Antigen-Specific Immune Responses through the expression of Chemokines," Journal Of Clinical Investigation, The American Society For Clinical Investigation, Inc., Sep. 1998, vol. 102, No. 6, pp. 1112-1124.

Kogkopoulou O., et al., "Conditional Up-Regulation of IL-2 Production By p38 MAPK Inactivation Is Mediated By Increased ERKI/2 Activity," Journal of Leukocyte Biology, May 2006, vol. 79, pp. 1052-1060.

Kokkoli E., et al., "Self-assembly and Applications of Biomimetic and Bioactive Peptide-amphiphiles," Soft Matter, 2006, vol. 2, pp. 1015-1024.

Korsholm , "Unravelling the Adjuvant Mechanism of Cationic Liposomes," Statens Serum Institute, Jun. 2006, pp. 15.00-15.30.

Korsholm K.S., et al., "The Adjuvant Mechanism of Dimethyldioctadecyl-ammonium Liposomes," Immunology, Jun. 2007, vol. 121, No. 2, pp. 216-226.

Kranz L.M., et al., "Systemic RNA Delivery to Dendritic Cells Exploits Antiviral Defence for Cancer Immunotherapy," Nature, Jun. 16, 2016, vol. 534, 16 Pages, DOI:10.1038/nature18300, XP055565453.

Li S., et al., "Targeted Delivery of Antisense Oligodeoxynucleotide and Small Interference RNA Into Lung Cancer Cells," Molecular Pharmaceutics, American Chemical Society, 2006, vol. 3, No. 5, pp. 579-588.

Liang M.T., et al., "Encapsulation of Lipopeptides Within Liposomes: Effect of Number of Lipid Chains, Chain Length and Method of Liposome Preparation," International Journal of Pharmaceutics, Elsevier B.V., 2005, vol. 301, pp. 247-254.

Lodoen M.B., et al., "Natural Killer Cells as an Initial Defense Against Pathogens," Current Opinion in Immunology, Elsevier Ltd, 2006, vol. 18, pp. 391-398.

Lonez C., et al., "Cationic Liposomal Lipids: From Gene Carriers to Cell Signaling," Progress in Lipid Research, 2008, vol. 47, pp. 340-347.

Lucas W., et al., "Viral Capsids and Envelopes: Structure and Function," Encyclopedia of Life Sciences (ELS), John Wiley & Sons, 2010, pp. 1-7.

Mackay C.R., "Chemokines: Immunology's High Impact Factors," Nature Immunology, Feb. 2001, vol. 2, No. 2, pp. 95-101.

Mansour M., et al., "Therapy Of Established B16-f10 Melanoma Tumors By A Single Vaccination Of Ctl/t Helper Peptides In Vaccimax," Journal of Translational Medicine, 2007, vol. 5, No. 20, 8 Pages.

Melief C.J.M., et al., "Effective Therapeutic Anticancer Vaccines Based on Precision Guiding of Cytolytic T Lymphocytes," Blackwell Munksgaard, Immunological Reviews, 2002, vol. 188, pp. 177-182.

Minutello M., et al., "Safety And Immunogenicity Of An Inactivated Subunit Influenza Virus Vaccine Combined With MF59 Adjuvant Emulsion In Elderly Subjects," Immunized For Three Consecutive Influenza Seasons, Vaccine, Elsevier Science Limited, 1999, vol. 17, pp. 99-104.

(56) References Cited

OTHER PUBLICATIONS

Moingeon P., et al., "Towards the Rational Design of Th1 Adjuvants," Vaccine, Elsevier Science Limited, 2001, vol. 19, pp. 4363-4372.
Non Final Office Action for Counterpart mailed Mar. 5, 2020 for U.S. Appl. No. 16/532,728, 12 Pages.
Non Final Office Action mailed Apr. 29, 2022 for U.S. Appl. No. 14/531,469, 12 Pages.
Non-Final Office Action from Counterpart U.S. Appl. No. 15/775,680, mailed Apr. 1, 2020, 14 Pages.
Notification of Reason of Rejection of Japanese Application No. JP2017218514, mailed Aug. 21, 2018, 13 pages.
Office Action for Canadian Application No. 2885741, dated May 10, 2022, 03 pages.
Office Action for European Application No. 08799629.4, mailed Aug. 7, 2012, 4 Pages.
Office Action for European Application No. 08799629.4, mailed Jan. 10, 2014, 3 Pages.
Office Action for European Application No. 08799629.4, mailed May 17, 2010, 1 Page.
Office Action for European Application No. 08799629.4, mailed Apr. 26, 2011, 3 Pages.
Office Action for European Application No. 09733034.4, mailed Apr. 16, 2015, 5 Pages.
Office Action for European Application No. 09733034.4, mailed Nov. 18, 2016, 4 Pages.
Office Action for European Application No. 12831495.2, mailed Dec. 1, 2016, 4 Pages.
Office Action for European Application No. 12831495.2, mailed Jun. 6, 2016, 5 Pages.
Office Action for European Application No. 12831495.2, mailed May 11, 2017, 4 Pages.
Office Action for European Application No. 13804165.2, mailed Mar. 2, 2018, 3 Pages.
Office Action for European Application No. 13804165.2, mailed Jul. 5, 2017, 4 Pages.
Office Action for European Application No. 13804165.2, mailed May 17, 2018, 3 Pages.
Office Action for European Application No. 13804165.2, mailed Sep. 22, 2016, 3 Pages.
Office Action for European Application No. 13804165.2, mailed Aug. 23, 2018, 3 Pages.
Office Action for European Application No. 13839199.0, mailed Nov. 13, 2017, 4 Pages.
Office Action for European Application No. 13839199.0, mailed Nov. 21, 2016, 4 Pages.
Office Action for European Application No. 13839199.0, mailed Jul. 30, 2018, 4 Pages.
Office Action for European Application No. 16865201.4, mailed on Jul. 16, 2020, 5 Pages.
Office Action for European Application No. 19203293.6, mailed Feb. 19, 2021, 4 Pages.
Office Action for European Application No. 19203293.6, mailed Dec. 22, 2021, 4 Pages.
Office Action for Taiwanese Application No. TW101133392, with English Translation, mailed Jul. 17, 2017, 05 pages.
Office Action from Corresponding Indian Application No. 7544/DELNP/2010, dated Jun. 22, 2017, 10 Pages.
Office Action from Counterpart Brazilian Patent Application. No. PI0910464-0, dated Nov. 6, 2018, and a Brief Summary in English, 5 pages.
Office Action of European Application No. 12831495.2, mailed Nov. 17, 2015, 5 pages.
Office Action of Taiwanese Application No. 101133392, dated May 16, 2016, along with an English translation of the Search Report, 8 pages.
Okada N., et al., "Effects of Lipofectin-Antigen Complexes on Major Histocompatibility Complex Class I-Restricted Antigen Presentation Pathway in Murine Dendritic Cells and on Dendritic Cell Maturation," Biochimica et Biophysica Acta, Elsevier Science, 2001, vol. 1527, pp. 97-101.
Oliveira L.M.F.D., et al., "Design of Immune Responses and Anti-Tumor Potential of an HPV16 E6E7 Multi-Epitope Vaccine," PLoS ONE, 2015, vol. 10, No. 9: e0138686, 13 Pages.
Padron-Regalado E., "Vaccine for SARS-CoV-2: Lessons from Other Coronavirus Strains," Infectious Diseases and Therapeutics, 2020, vol. 9, pp. 255-274.
Pialoux G.D., et al., "Lipopeptides Induce Cell-Mediated Anti-HIV Immune Responses In Seronegative Volunteers," Lippincott Williams & Wilkins, Inc., Official Journal Of The International Of AIDS, Jul. 6, 2001, vol. 15, No. 10, pp. 1239-1249.
Pierre Y., et al., "Liposome-Mediated DNA Immunisation via the Subcutaneous Route," Journal of Drug Targeting, Taylor & Francis Ltd, 2003, vol. 11, No. 8-10, pp. 555-563.
Radu C.G., et al., "T Cell Chemotaxis to Lysophosphatidylcholine through the G2A Receptor," Proceedings of the National Academy of Sciences, The National Academy of Sciences of The USA, Jan. 6, 2004, vol. 101, No. 1, pp. 245-250.
Rao P.E., et al., "Differentiation and Expansion of T Cells with Regulatory Function from Human Peripheral Lymphocytes by Stimulation in the Presence of TGF-B," The Journal of Immunology, The American Association of Immunologists, Inc., 2005, vol. 174, pp. 1446-1455.
Restriction Requirement from Counterpart dated Jan. 7, 2020 for U.S. Appl. No. 15/775,680, 09 Pages.
Riemer A.B., et al., "A Conserved E7-Derived Cytotoxic T Lymphocyte Epitope Expressed On Human Papillomavirus-16 Transformed HLA-A2+ Human Epithelial Cancers," The Journal Of Biological Chemistry, Sep. 17, 2010, vol. 285, No. 38, pp. 29608-29622, XP055207597.
Robinson J.H., et al., "Palmitic Acid Conjugation of a Protein Antigen Enhances Major Histocompatibility Complex Class II-Restricted Presentation to T Cells," Immunology, 1992, vol. 76, pp. 593-598.
Rock K.L., et al., "Natural Endogenous Adjuvants," Spriner Semin Immunology, 26, 2005, pp. 231-246.
Ross T.M., "A Trivalent Virus-like Particle Vaccine Elicits Protective Immune Responses against Seasonal Influenza Strains in Mice and Ferrets," PloS one, e6032, Jun. 24, 2009, vol. 4, No. 6, pp. 1-11.
Rughetti A., et al., "Transfected Human Dendritic Cells to Induce Antitumor Immunity," Gene Therapy, Sep. 2000, vol. 7. No. 17, pp. 1458-1466.
Santin A.D., et al., "Induction of Human Papillomavirus-Specific CD4+ and CDS+ Lymphocytes by E7-Pulsed Autologous Dendritic Cells in Patients with Human Papillomavirus Type 16- and 18-Positive Cervical Cancer," Journal of Virology, Jul. 1999, vol. 73, No. 7, pp. 5402-5410.
Sato N., et al., "CC Chemokine Receptor (CCR) 2 Is Required For Langhans Cell Migration And Localization Of T Helper Cell Type 1 (Th1)-Inducing Dendritic Cells: Absence Of CCR2 Shifts The Leishmania Major-Resistant Phenotype To A Susceptible State Dominated By Th2 Cytokines, B Cell Outgrowth, And Sustained Neutrophilic Inflammation," Journal Of Experimental Medicine, The Rockefeller University Press, Jul. 17, 2000, vol. 192, No. 2, pp. 205-218.
Schroeder M.A., et al., "Pegylated Murine GM-CSF Increases Myeloid Derived Suppressor Cells In Vivo," Blood, 2011, vol. 118, No. 21, p. 2967, ISSN: 0003513278.
Second Examiner's Report and Examination Search Report from Counterpart Canadian Patent Application No. 2,885,741, dated Aug. 10, 2020, 4 Pages.
Second Office Action and Supplementary Search Report for Corresponding Chinese Application No. 201380060902.8, dated Mar. 31, 2017, 28 Pages.
Shimizu T., et al., "Antitumor Activity, Mitogenicity, and Lethal Toxicity of Chemical Synthesized Monosaccharide Analog of Lipid A," J. Pharmacobiodyn, 1988, vol. 11, No. 7, pp. 512-518.
Shinozaki Y., et al., "Tumor-specific Cytotoxic T Cell Generation And Dendritic Cell Function Are Differentially Regulated By Interleukin 27 During Development Of Anti-tumor Immunity," International Journal of Cancer, 2009, vol. 124, No. 6, pp. 1372-1378.

(56) References Cited

OTHER PUBLICATIONS

Song Y.K., et al., "Free Liposomes Enhance the Transfection Activity of DNA/Lipid Complexes in Vivo by Intravenous Administration," Biochimica et Biophysica Acta, 1998, vol. 1372, pp. 141-150.
Sprott G.D., et al., "Activation of Dendritic Cells by Liposomes Prepared from Phosphatidylinositol Mannosides from Mycobacterium Bovis Bacillus Calmette-Guerin and Adjuvant Activity In Vivo," Infection and Immunity, Sep. 2004, vol. 72, No. 9, pp. 5235-5246.
Steller M.A., et al., "Cell-Mediated Immunological Responses in Cervical and Vaginal Cancer Patients Immunized with a Lipidated Epitope of Human Papillomavirus Type 16 E7," Clinical Cancer Research, Sep. 1998, vol. 4, pp. 2103-2109.
Sumida S.M., et al., "Recruitment and Expansion of Dendritic Cells In Vivo Potentiate the Immunogenicity of Plasmid DNA Vaccines," The Journal of Clinical Investigation, USA, Nov. 2004, vol. 114, No. 9, pp. 1334-1342.
Sun W.Q., et al., "Stability of Dry Liposomes in Sugar Glasses," Biophysical Journal, Apr. 1996, vol. 70, pp. 1769-1776.
Taiwan Search Report for Taiwanese Application No. 107143751, dated Jul. 27, 2022, 2 Pages, with translation.
Takaoka A., et al., "Integration of interferon-Alpha/Beta Signaling to P53 Responses in Tumor Suppression and Antiviral Defense," Nature, Jul. 31, 2003, vol. 424, pp. 516-523.
The Notice of Reasons for Rejection of Counterpart Japanese Patent Application No. 2019-518245, mailed Oct. 26, 2021, Along With an English Translation, 14 Pages.
Third Examiner's Report and Examination Search Report from Counterpart Canadian Patent Application No. 2,885,741, dated Jun. 30, 2021, Along with A Request to Withdraw Report dated Aug. 25, 2021, 5 Pages.
Tindle R., et al., "NCBI Blast Search Teaching Sequence 43," Genback, U.S. Pat. No. 6,183,745, 2001, 1 Page.
Tobiume K., et al., "ASK1 Is Required For Sustained Activations Of JNL/p38 MAP Kinases And Apoptosis," EMBO Reports, European Molecular Biology Organization, 2001, vol. 2, No. 3, pp. 222-228.
Toledo H., et al., "A Phase I Clinical Trial of a Multi-Epitope Polypeptide TAB9 Combined with Montanide ISA720 Adjuvant in Non-HIV-1 Infected Human Volunteers," Vaccine, Elsevier Science Ltd, 2001, vol. 19, pp. 4328-4336.
Translation of Notification of Reason for Rejection from Corresponding Japanese Patent Application No. 2013-217819, mailed Jan. 10, 2017, 7 Pages.
"Transplantation," Supplement 1, 2010, vol. 90, No. 2S, pp. 519-2687, 1 Page, ISSN: 0003513279.
Tsang K.Y., et al., "Identification and Characterization of Enhancer Agonist Human Cytotoxic T-cell Epitopes of The Human Papillomavirus Type 16 (Hpv16) E6/E7," Vaccine, 2017, vol. 35, pp. 2605-2611.
Uemura A., et al., "Induction Of Immune Responses Against Glycosphingolipid Antigens: Comparison Of Antibody Responses In Mice Immunized With Antigen Associated With Liposomes Prepared From Various Phospholipids," Journal Of Veterinary Medical Science, 2005, vol. 67, No. 12, pp. 1197-1201.
United States Patent and Trademark Office, Offic Action for U.S. Appl. No. 11/121,840, mailed Sep. 7, 2007, 6 Pages.
United States Patent and Trademark Office, Office Action for U.S. Appl. No. 11/121,840, mailed Jun. 4, 2007, 5 Pages.
Varypataki E.M., et al., "Cationic Liposomes Loaded With a Synthetic Long Peptide and Poly(L:C): a Defined Adjuvanted Vaccine for Induction Of Antigen-Specific T Cell Cytotoxicity," The AAPS Journal, Jan. 2015, vol. 17, No. 1, pp. 216-226.
Vasievich E. A., et al., "Enantiospecific Adjuvant Activity of Cationic Lipid DOTAP in Cancer Vaccine", Cancer Immunology, Immunotherapy, May 2011, vol. 60, No. 5, Abstract Only, 1 Page.
Vasievich E.A., et al., "Enantiospecific Adjuvant Activity of Cationic Lipid DOTAP In Cancer Vaccine," Cancer Immunology, Immunotherapy, May 1, 2011, vol. 60, No. 5, pp. 629-638, DOI:10. 1007/s00262-011-0970-1, ISSN 0340-7004, XP055057926.
Vautier-Giongo C., et al., "Effects Of Interactions On The Formation Of Mixed Micelles Of 1.2-diheptaoyl-sn-glycero-3-phosphocholine With Sodiumdodecyl Sulfate And Dodecyltrimethylemmonuium Bromide," Journal of Colloid and Interface Science 282, 2005, pp. 149-155.
Verheul A.F.M., et al., "Monopalmitic Acid-Peptide Conjugates Induce Cytotoxic T Cell Responses Against Malarial Epitopes: Importance of Spacer Amino Acids," Journal of Immunological Methods, Elsevier Science B.V., 1995, vol. 182, pp. 219-226.
Vogel F.R., et al., "A Compendium of Vaccine Adjuvants and Excipients," Pharmaceutical biotechnology, 1995, vol. 6, 89 Pages.
Vogel F.R., "Improving Vaccine Performance With Adjuvants," Clinical Infectious Diseases, Infectious Diseases Society Of America, 2000, vol. 30, Suppl. 3, pp. S266-S270.
Walker C., et al., "Cationic Lipids Direct A Viral Glycoprotein Into The Class I Major Histocompatibility Complex Antigen-presentation Pathway," Proceedings of National Acadamy Science, USA, Sep. 1992, vol. 89, pp. 7915-7918.
Wang H., et al., "Potential Involvement Of Monocyte Chemoattractant Protein (MCP)-1/CCL2 In IL-4-Mediated Tumor Immunity Through Inducing Dendritic Cell Migration Into The Draining Lymph Nodes," International Immunopharmacology, Elsevier Science B.V, 2003, vol. 03, pp. 627-642.
Wang L., et al., "Lysophosphatidylcholine-Induced Surface Redistribution Regulates Signaling Of The Murine G Protein-Coupled Receptor G2A," Molecular Biology Of The Cell, The American Society For Cell Biology, May 2005, vol. 16, pp. 2234-2247.
Wang R-F., et al., "Enhancement of Antitumor Immunity By Prolonging Antigen Presentation on Dendritic Cells," Nature Biotechnology, Nature Publishing Group, Feb. 2002, vol. 20, pp. 149-154.
Weiss A., et al., "Intracellular Peptide Delivery Using Amphiphilic Lipid-Based Formulations," Biotechnology and Bioengineering, US, Oct. 2011, (20110425), vol. 108, No. 10, pp. 2477-2487, DOI: 10.1002/bit.23182, ISSN 0006-3592, XP055250096.
Welters M.J.P., et al., "Induction of Tumor-Specific CD4+ and CD8+ T-Cell Immunity in Cervical Cancer Patients by a Human Papillomavirus Type 16 E6 and E7 Long Peptides Vaccine," Clinical Cancer Research, Jan. 1, 2008, vol. 14, No. 1, pp. 178-187.
Wenworth D.E., et al., "Hemagglutinin [Influenza A virus (A/New Caledonia/20/1999(H1N1))]," GenBank Accession # AFO65027, Jul. 26, 2012, 2 Pages.
Whitmore M., et al., "LPD Lipopolyplex Initiates A Potent Cytokine Response And Inhibits Tumor Growth," Gene Therapy, Stockton Press, 1999, vol. 6, pp. 1867-1875.
Wrapp D., et al., "Cryo-EM Structure of the 2019-nCoV Spike in the Prefusion Conformation," Science, Mar. 13, 2020, vol. 367, pp. 1260-1263.
Xiao X., et al., "HLA-A, HLA-B, HLA-DRB1 Polymorphisms and Risk of Cervical Squamous Epithelial Cell Carcinoma: A Population Study in China," Asian Pacific Journal of Cancer Prevention, 2013, vol. 14, No. 7, pp. 4427-4433, XP055497830.
Yamshchikov G.V., et al., "Evaluation Of Peptide Vaccine Immunogenicity In Draining Lymph Nodes And Peripheral Blood Of Melanoma Patients," International Journal of Immunology, Wiley-Liss, Inc., 2001, vol. 92, pp. 703-711.
Yan W., et al., "Mechanism of Adjuvant Activity of Cationic Liposome: Phosphorylation of A Map Kinase, ERK and Induction of Chemokines," Molecular Immunology, 2007, vol. 44, pp. 3672-3681.
Yao T., et al., "Integrated Basic Chemistry for Geo Science," Naniing University Press, 2007, pp. 410-421.
Yao Y., et al., "HPV-16 E6 and E7 Protein T Cell Epitopes Prediction Analysis Based on Distributions of HLA-A Loci Across Populations: An in Silico Approach," Vaccine, 2013, vol. 31, No. 18, pp. 2289-2294, XP055497828.
Yasuda K., et al., "Endosomal Translocation of Vertebrate DNA Activates Dendritic Cells via TLR9-Dependent and Independent Pathways," The Journal of Immunology, 2005, vol. 174, pp. 6129-6136.
Yoo J.K., et al., "IL-18 Induces Monocyte Chemotactic Protein-1 Production in Macrophages Through the Phosphatidylinositol 3-Kinase/

(56) References Cited

OTHER PUBLICATIONS

Akt and MEK/ERK1/2 Pathways," The Journal of Immunology, The American Association of Immunologists Incorporated, 2005, vol. 175, pp. 8280-8286.

Yoshimura T., et al., "Human Monocyte Chemoattractant Protein-1 (MCP-1), Full Length cDNA Cloning, Expression In Mitogen-Stimulated Blood Mononuclear Leukocytes, and Sequence Similarity To Mouse Competence Gene JE," Federation of European Biochemical Societies, Elsevier Science Publishers B.V., Feb. 1989, vol. 244, No. 2, pp. 487-493.

Yotsumoto S., et al., "Endosomal Translocation of CpG-Oligodeoxynucleotides Inhibits DNA-PKcs-Dependent IL-10 Production in Macrophages," The Journal of Immunology, 2008, vol. 180, pp. 809-816.

Yu H., et al., "Novel Chlamydia Muridarum T Cell Antigens Induce Protective Immunity Against Lung and Genital Tract Infection in Murine Models," The Journal of Immunology, 2009, vol. 182, pp. 1602-1608.

Yu J.J., et al., "Regulation and Phenotype of an Innate Th1 Cell: Role of Cytokines and the P38 Kinase Pathway," The Journal of Immunology, The American Association of Immunologists, 2003, vol. 171, pp. 6112-6118.

Zaks K., et al., "Efficient Immunization and Cross-Priming by Vaccine Adjuvants Containing TLR3 or TLR9 Agonists Complexed to Cationic Liposomes," The Journal of Immunology, 2006, vol. 176, pp. 7335-7345.

Zhang H., et al., "English Translation of Specification of CN111217918," European Patent Office, 2020, 85 pages.

Zhang H., et al., "Stress-Induced Inhibition of ERK1 and ERK2 by Direct Interaction With p38 MAP Kinase," The Journal of Biological Chemistry, The American Society for Biochemistry and Molecular BiologyInc, Mar. 9, 2001, vol. 276, No. 10, pp. 6905-6908.

Zhang L., et al., "Converting Peptides into Drug Leads by Lipidation," Current Medicinal Chemistry, 2012, vol. 19, No. 11, pp. 1602-1618, ISSN 0929-8673.

Zhao L-J., et al., "Interferon Alpha Regulates MAPK and STAT1 Pathways in Human Hepatoma Cells," Virology Journal, Apr. 6, 2011, vol. 8, No. 157, pp. 1-7.

Zitvogel L., et al., "Type I Interferons in Anticancer Immunity," Nature Reviews Immunology, Jul. 2015, vol. 15, pp. 405-414.

Third Examiner's Report from corresponding Canadian Patent Application No. 2,876,656 dated Mar. 25, 2021.

US Non-Final Office Action in U.S. Appl. No. 14/531,469, dated Mar. 10, 2023, 13 pages.

US Non-Final Office Action in U.S. Appl. No. 16/532,613, dated Mar. 17, 2023, 120 pages.

US Non-Final Office Action in U.S. Appl. No. 16/899,763, dated Mar. 16, 2023, 52 pages.

Lonez, et al., Cationic Lipids Activate Intracellular Signaling Pathways, Advanced Drug Delivery Reviews, 2012, 64(15), pp. 1749-1758.

Office Action for Korean Patent Application No. 10 2019 7012979, mailed Oct. 25, 2022, 11 Pages (with English translation).

Office Action for Taiwan Patent Application No. 107143751, mailed Aug. 1, 2022, 13 Pages (with English translation).

Wang, et al., Classification of Human Leukocyte Antigen (HLA) Supertypes, Immunoinformatics, Methods in Molecular Biology, 2014, vol. 1184, pp. 309-317.

Bo L., "Research Progress on Therapeutic Vaccines for Human Papillomavirus," Acta Academiae Medicinae Sinicae, vol. 29, Issue 05, Oct. 31, 2017, pp. 685-690.

Dalby et al., Advanced transfection with Lipofectamine 2000 reagent: primary neurons, siRNA, and High-throughput applications, Methods, 2004, 33: 95-103.

Gandhapudi S.K., et al., "Recombinant Protein Vaccines Formulated with Enantio Specific Cationic Lipid R DOTAP Induce Protective Cellular and Antibody Mediated Immune Responses in Mice," Viruses, Feb. 4, 2023, vol. 15, No. 432, pp. 1 22.

Henson T.R., et al., "R DOTAP Cationic Lipid Nanoparticles Outperform Squalene Based Adjuvant Systems in Elicitation of CD4 T Cells after Recombinant Influenza Hemagglutinin Vaccination," Viruses, Feb. 15, 2023, vol. 15, No. 538, pp. 1 14.

Johnson R.K., et al., "The Clinical Impact of Screening and Other Experimental Tumor Studies," Cancer Treatment Reviews, 1975, vol. 2, pp. 1 31.

Kornek M., et al., "1,2-Dioleoyl-3-Trimethylammonium-Propane (DOTAP)-Formulated, Immune-Stimulatory Vascular Endothelial Growth Factor A Small Interfering RNA (siRNA) Increases Antitumoral Efficacy in Murine Orthotopic Hepatocellular Carcinoma with Liver Fibrosis," Molecular Medicine, 2008, vol. 14, No. 7-8, pp. 365-373.

Office Action for Japanese Application No. 20200531050, mailed Sep. 12, 2023, 21 Pages.

Office Action for Korean Patent Application No. 10-2020-7019224, dated Mar. 26, 2024, 14 pages.

Persano S., et al., "Lipopolyplex Potentiates Anti-Tumor Immunity of mRNA-based Vaccination," Biomaterials, Feb. 2017, vol. 125, pp. 81-89.

Sayour E.J., et al. "Systemic activation of antigen-presenting cells via RNA-loaded nanoparticles," Oncolmmunology, Jan. 2017, vol. 6, No. 1, 15 pages.

SEQUENCE LISTING

<160> NUMBER OF SEQ ID NOS: 13

<210> SEQ ID NO 1
<211> LENGTH: 9
<212> TYPE: PRT
<213> ORGANISM: Artificial Sequence

```
<220> FEATURE:
<223> OTHER INFORMATION: Synthetic

<400> SEQUENCE: 1

Arg Ala His Tyr Asn Ile Val Thr Phe
1               5

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Gly Gln Ala Glu Pro Asp Arg Ala His Tyr Asn Ile Val Thr Phe
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Lys Ser Ser Gly Gln Ala Glu Pro Asp Arg Ala His Tyr Asn Ile Val
1               5                   10                  15

Thr Phe

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Tyr Met Leu Asp Leu Gln Pro Glu Thr Thr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Lys Ser Ser Tyr Met Leu Asp Leu Gln Pro Glu Thr Thr
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Synthetic

<400> SEQUENCE: 6

Met His Gly Asp Thr Pro Thr Leu His Glu Tyr Met Leu Asp Leu Gln
1               5                   10                  15

Pro Glu Thr Thr
            20
```

```
<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

Leu Leu Met Gly Thr Leu Gly Ile Val Cys Pro Ile Cys Ser Gln Lys
1               5                   10                  15
Pro

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Lys Val Pro Arg Asn Gln Asp Trp Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ser Tyr Val Asp Phe Phe Val Trp Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Lys Tyr Ile Cys Asn Ser Ser Cys Met
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Lys Ser Ser Lys Val Pro Arg Asn Gln Asp Trp Leu
1               5                   10

<210> SEQ ID NO 12
<211> LENGTH: 23
<212> TYPE: PRT
<213> ORGANISM: Artificial Sequence
<220> FEATURE:
<223> OTHER INFORMATION: Synthetic

<400> SEQUENCE: 12

Lys Ser Ser Met His Gly Asp Thr Pro Thr Leu His Glu Tyr Met Leu
1               5                   10                  15
```

```
Asp Leu Gln Pro Glu Thr Thr
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic

<400> SEQUENCE: 13

Lys Ser Ser Leu Leu Met Gly Thr Leu Gly Ile Val Cys Pro Ile Cys
1               5                   10                  15

Ser Gln Lys Pro
            20
```

METHODS OF MODULATING IMMUNE RESPONSES WITH CATIONIC LIPID VACCINE COMPOSITIONS

GOVERNMENT RIGHTS

Part of the work leading to this invention was carried out with the United States Government support provided under the National Institutes of Health CRADA No. 2644. Therefore, the United States Government has certain rights in and to the present invention.

INCORPORATION OF SEQUENCE LISTING

The material in the accompanying sequence listing is hereby incorporated by reference into this application. The accompanying sequence listing text file, name PDS_16_1046WO_US_DIV_CON_Sequence_Listing_ST25.txt, was created on Oct. 2, 2020, and is 4 kb. The file can be accessed using Microsoft Word on a computer that uses Windows OS.

TECHNICAL FIELD

Development of safe and effective immunotherapies and therapeutic vaccines for human use remains an important medical need for patients worldwide. Typically, a vaccine composition includes an antigen to stimulate a targeted immune response. However, some developmental vaccines are ineffective because they are weak stimulators of an immune response in a broad mammalian population. For example, the antigen in the vaccine composition may be poorly immunogenic in the mammal. In addition, some vaccines may not efficiently deliver antigens to the antigen presenting cells ("APCs") of the mammal's immune system.

Myeloid-derived suppressor cells (MDSCs) are a heterogeneous population of early myeloid progenitors which have the capacity to suppress the adaptive immune response in patients, such as response mediated by $CD4^+$ and $CD8^+$ T cells. MDSCs are known to secrete immunosuppressive cytokines and induce regulatory T cell development. Furthermore, MDSCs are induced by pro-inflammatory cytokines and are found in increased numbers in infectious and in inflammatory pathological conditions.

MDSCs accumulate in the blood, bone marrow, and secondary lymphoid organs of tumor-bearing mice and their presence in the tumor microenvironment has been suggested to have a causative role in promoting tumor-associated immune suppression. Importantly, tumor antigen-specific T-cell tolerance has been reported to be a critical element of tumor escape.

Furthermore, MDSCs have been found to be present in most cancer patients. Significant research is currently being conducted within the industry to identify a means of inhibiting immune suppressive cells, for example MDSCs and T-regulatory cells, as a means of improving the T-cell responses to attack and kill the infected cells. Current practice in the industry focuses on exploring the use of blocking antibodies to block and inhibit relevant immune suppressive factors. A vaccine such as the human antibody Ipilimumab may be used to block cytotoxic T-lymphocyte associated antigen-4 (CTLA-4), known to play a role in regulating immune responses as a therapeutic vaccine to treat melanoma.

BACKGROUND AND SUMMARY OF THE INVENTION

Vaccines also typically include adjuvants in an attempt to enhance the efficacy of antigens in the vaccine composition. For example, adjuvants such as water-in-oil emulsions, alum (e.g., aluminum salts), and other chemicals are typically utilized to enhance antigen response in a mammal. In addition to traditional adjuvants, other adjuvants with intrinsic immune effects (e.g., influenza virosomes and Chiron's MF59) may be used. However, these adjuvants are also undesirable because evidence from animal models (according to clinical trial reports on HSV and influenza vaccines) suggests that they merely enhance production of neutralizing antibodies rather than enhancing T-cell responses in animals.

Therefore, there exists a need for new vaccine compositions that effectively deliver antigens or promote antigen uptake by the antigen presenting cells in order to stimulate an immune response in a mammal, as well inhibiting immune suppressive cells to improve the immune response in a mammal. Moreover, new and effective methods of stimulating cell mediated immune responses in mammals, possibly by including a safe and effective immunologic modifier ("immunomodulator") in a vaccine composition along with a therapeutic factor, are also very desirable. Accordingly, the present disclosure provides vaccine compositions and method of using the compositions that exhibit desirable properties and provide related advantages for improvement in reducing an immune suppressor cell population and augmenting an immune response in a mammal.

The present disclosure provides vaccine compositions comprising at least one adjuvant and at least one therapeutic factor. The disclosure also provides methods of reducing an immune suppressor cell population in a mammal, methods of augmenting an immune response in a mammal, and methods of treating a disease in a mammal utilizing the vaccine compositions.

The vaccine compositions and methods according to the present disclosure provide several advantages compared to other compositions and methods in the art. First, the vaccine compositions include an adjuvant that is an immunomodulator to enhance, direct, or promote an appropriate immune response in a mammal. Immunomodulators have the potential to effectively boost a mammal's immune response to antigens if they are included in a vaccine composition. For example, an immunomodulator may advantageously accomplish one or more of the following: (1) improve antigen delivery and/or processing in the APC, (2) induce the production of immunomodulatory cytokines that favor the development of immune responses to the antigen, thus promoting cell mediated immunity, including cytotoxic T-lymphocytes ("CTL"), (3) reduce the number of immunizations or the amount of antigen required for an effective vaccine, (4) increase the biological or immunological half-life of the vaccine antigen, and (5) overcome immune tolerance to antigen by inhibiting immune suppressive factors. In some embodiments, cationic lipid-based adjuvants may be utilized potent immunomodifying adjuvants and can elicit superior T-cell and antibody immune responses in vaccine compositions.

Second, the vaccine compositions in the current disclosure include a therapeutic factor such as a cytokine that as a combination can reduce an immune suppressor cell population in a mammal, which can improve the immune response of a mammal in response to disease. Current research to identify means to inhibit immune suppressive cells such as MDSC and T-regulatory cells utilize complex blocking antibodies. Consequently, administration of a potent vaccine composition including a therapeutic factor such as a cytokine can be easier to administer to a patient and improve immune response, particularly in tumors.

Third, the vaccine compositions in the current disclosure including a therapeutic factor can cause a reduction in MDSC both with and without a disease-specific antigen, thus resulting in a unique and powerful approach to treating diseases such as cancer by facilitating the natural activation of antigen-specific T-cells while simultaneously reducing the immune suppressor cell population. The vaccine compositions including a therapeutic factor result in the generation of superior disease-specific immune responses, which are not observed when either the adjuvant or the therapeutic factor alone is formulated with the antigen.

Finally, the therapeutic factor, when combined with cationic lipid adjuvant to form the vaccine composition, results in a unique synergistic improvement in immune response in a mammal. Combinations of therapeutic factor (e.g., GM-CSF) with other adjuvants (e.g., incomplete Freund's adjuvant (IFA) or anti-CD40+IFA) do not result in similar synergistic improvement in immune response. Therefore, the combination of the cationic lipid adjuvant and the therapeutic factor specifically and significantly result in a synergistic improvement in immune response that cannot be replicated using other commonly used adjuvants.

The following numbered embodiments are contemplated and are non-limiting:

1. A vaccine composition comprising an adjuvant and a therapeutic factor.
2. The vaccine composition of clause 1, wherein the adjuvant is an immunomodulator.
3. The vaccine composition of clause 1 or clause 2, wherein the adjuvant is a cationic lipid.
4. The vaccine composition of clause 3, wherein the cationic lipid is purified.
5. The vaccine composition of clause 3 or clause 4, wherein the cationic lipid is selected from the group consisting of DOTAP, DOTMA, DOEPC, and combinations thereof.
6. The vaccine composition of any one of clauses 3 to 5, wherein the cationic lipid is DOTAP.
7. The vaccine composition of any one of clauses 3 to 5, wherein the cationic lipid is DOTMA.
8. The vaccine composition of any one of clauses 3 to 5, wherein the cationic lipid is DOEPC.
9. The vaccine composition of clause 1 or clause 2, wherein the adjuvant is an enantiomer of a cationic lipid.
10. The vaccine composition of clause 9, wherein the enantiomer is purified.
11. The vaccine composition of clause 9 or clause 10, wherein the enantiomer is R-DOTAP or S-DOTAP.
12. The vaccine composition of clause 9 or clause 10, wherein the enantiomer is R-DOTAP.
13. The vaccine composition of clause 9 or clause 10, wherein the enantiomer is S-DOTAP.
14. The vaccine composition of clause 9 or clause 10, wherein the enantiomer is R-DOTMA or S-DOTMA.
15. The vaccine composition of clause 9 or clause 10, wherein the enantiomer is R-DOTMA.
16. The vaccine composition of clause 9 or clause 10, wherein the enantiomer is S-DOTMA.
17. The vaccine composition of clause 9 or clause 10, wherein the enantiomer is R-DOEPC or S-DOEPC.
18. The vaccine composition of clause 9 or clause 10, wherein the enantiomer is R-DOEPC.
19. The vaccine composition of clause 9 or clause 10, wherein the enantiomer is S-DOEPC.
20. The vaccine composition of any one of clauses 1 to 19, wherein the therapeutic factor is selected from the group consisting of interleukins 1-18, stem cell factor, basic FGF, EGF, G-CSF, GM-CSF, FLK-2 ligand, HILDA, MIP-1a, TGF-β, TGF-α, M-CSF, IFN-γ, IFN-α, IFN-β, soluble CD23, LIF, and combinations thereof.
21. The vaccine composition of any one of clauses 1 to 19, wherein the therapeutic factor is a cytokine.
22. The vaccine composition of clause 20, wherein the cytokine is GM-CSF.
23. The vaccine composition of any one of clauses 1 to 19, wherein the therapeutic factor is an immune cell growth factor.
24. The vaccine composition of any one of clauses 1 to 23, wherein the composition further comprises one or more antigens.
25. The vaccine composition of clause 24, wherein one or more antigens is a protein-based antigen.
26. The vaccine composition of clause 24, wherein one or more antigens is a peptide-based antigen.
27. The vaccine composition of any one of clauses 24 to 26, wherein one or more antigens is selected from the group consisting of a cancer antigen, a viral antigen, a bacterial antigen, and a pathogenic antigen.
28. The vaccine composition of any one of clauses 24 to 26, wherein one or more antigens is a cancer antigen.
29. The vaccine composition of any one of clauses 24 to 26, wherein one or more antigens is a viral antigen.
30. The vaccine composition of any one of clauses 24 to 26, wherein one or more antigens is a bacterial antigen.
31. The vaccine composition of any one of clauses 24 to 26, wherein one or more antigens is a pathogenic antigen.
32. The vaccine composition of clause 31, wherein the pathogenic antigen is a synthetic or recombinant antigen.
33. The vaccine composition of any one of clauses 24 to 32, wherein at least one antigen is an HPV protein or peptide.
34. The vaccine composition of any one of clauses 24 to 33, wherein at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13).
35. The vaccine composition of any one of clauses 24 to 33, wherein at least one antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.
36. The vaccine composition of any one of clauses 24 to 33, wherein the antigens comprise one or more of the gp100 sequence (KVPRNQDWL [SEQ. ID. No. 8]) and the TRP2 sequence (SYVDFFVWL [SEQ. ID. No. 9]).
37. The vaccine composition of any one of clauses 24 to 33, wherein the antigen comprises the sequence RAHYNIVTF (SEQ. ID. NO: 1).

38. The vaccine composition of any one of clauses 24 to 33, wherein the antigen comprises the sequence GQAEPDRAHYNIVTF (SEQ. ID. NO: 2).
39. The vaccine composition of any one of clauses 24 to 33, wherein the antigen comprises the sequence KSSGQAEPDRAHYNIVTF (SEQ. ID. NO: 3).
40. The vaccine composition of any one of clauses 24 to 33, wherein the antigen comprises the sequence YMLDLQPETT (SEQ. ID. NO: 4).
41. The vaccine composition of any one of clauses 24 to 33, wherein the antigen comprises the sequence KSSYMLDLQPETT (SEQ. ID. NO: 5).
42. The vaccine composition of any one of clauses 24 to 33, wherein the antigen comprises the sequence MHGDTPTLHEYMLDLQPETT (SEQ. ID. NO: 6).
43. The vaccine composition of any one of clauses 24 to 33, wherein the antigen comprises the sequence LLMGTLGIVCPICSQKP (SEQ. ID. NO: 7).
44. The vaccine composition of any one of clauses 24 to 33, wherein the antigen comprises the sequence KVPRNQDWL (SEQ. ID. NO: 8).
45. The vaccine composition of any one of clauses 24 to 33, wherein the antigen comprises the sequence SYVDFFVWL (SEQ. ID. NO: 9).
46. The vaccine composition of any one of clauses 24 to 33, wherein the antigen comprises the sequence KYICNSSCM (SEQ. ID. NO: 10).
47. The vaccine composition of any one of clauses 24 to 33, wherein the antigen comprises the sequence KSSKVPRNQDWL (SEQ. ID. NO: 11).
48. The vaccine composition of any one of clauses 24 to 47, wherein at least one antigen is selected from the group consisting of a lipoprotein, a lipopeptide, and a protein or peptide modified with an amino acid sequence having an increased hydrophobicity or a decreased hydrophobicity.
49. The vaccine composition of any one of clauses 24 to 48, wherein one or more antigens is a lipidated antigen or an antigen modified to increase hydrophobicity of the antigen.
50. The vaccine composition of any one of clauses 24 to 49, wherein at least one antigen is a modified protein or peptide.
51. The vaccine composition of clause 50, wherein the modified protein or peptide is bonded to a hydrophobic group.
52. The vaccine composition of clause 51, wherein the modified protein or peptide bonded to a hydrophobic group further comprises a linker sequence between the antigen and the hydrophobic group.
53. The vaccine composition of clause 51 or 52, wherein the hydrophobic group is a palmitoyl group.
54. The vaccine composition of any one of clauses 24 to 53, wherein at least one antigen is an unmodified protein or peptide.
55. The vaccine composition of any one of clauses 1 to 54, wherein the vaccine composition induces an immune response in a mammal by activating the mitogen-activated protein (MAP) kinase signaling pathway.
56. The vaccine composition of clause 55, wherein the MAP kinase signaling pathway is activated by stimulating at least one of extracellular signal-regulated kinase ("ERK")-1, ERK-2, and p38.
57. The vaccine composition of any one of clauses 1 to 56, wherein the vaccine composition enhances functional antigen-specific CD8+ T lymphocyte response in a mammal.
58. The vaccine composition of clause 57, wherein the mammal is a human.
59. A method of reducing an immune suppressor cell population in a mammal, said method comprising the step of administering an effective amount of a vaccine composition to the mammal, wherein the vaccine composition comprises an adjuvant and a therapeutic factor.
60. The method of clause 59, wherein the immune suppressor cell is MDSC.
61. The method of clause 59, wherein the immune suppressor cell is a T regulatory cell.
62. The method of any one of clauses 59 to 61, wherein the reduction results in an increase in T-cell response in the mammal.
63. The method of clause 62, wherein the T-cell is a tumor-infiltrated T-cell.
64. The method of clause 62 or clause 63, wherein the T-cell response is a CD4+ T-cell response.
65. The method of clause 64, wherein the CD4+ T-cell is a tumor-infiltrated CD4+ T-cell.
66. The method of clause 62 or clause 63, wherein the T-cell response is a CD8+ T-cell response.
67. The method of clause 66, wherein the CD8+ T-cell is a tumor-infiltrated CD8+ T-cell.
68. The method of any one of clauses 59 to 67, wherein the mammal is a human.
69. The method of any one of clauses 59 to 68, wherein the adjuvant is an immunomodulator.
70. The method of any one of clauses 59 to 69, wherein the adjuvant is a cationic lipid.
71. The method of clause 70, wherein the cationic lipid is purified.
72. The method of clause 70 or clause 71, wherein the cationic lipid is selected from the group consisting of DOTAP, DOTMA, DOEPC, and combinations thereof.
73. The method of any one of clauses 70 to 72, wherein the cationic lipid is DOTAP.
74. The method of any one of clauses 70 to 72, wherein the cationic lipid is DOTMA.
75. The method of any one of clauses 70 to 72, wherein the cationic lipid is DOEPC.
76. The method of any one of clauses 59 to 69, wherein the adjuvant is an enantiomer of a cationic lipid.
77. The method of clause 76, wherein the enantiomer is purified.
78. The method of clause 76 or clause 77, wherein the enantiomer is R-DOTAP or S-DOTAP.
79. The method of clause 76 or clause 77, wherein the enantiomer is R-DOTAP.
80. The method of clause 76 or clause 77, wherein the enantiomer is S-DOTAP.
81. The method of clause 76 or clause 77, wherein the enantiomer is R-DOTMA or S-DOTMA.
82. The method of clause 76 or clause 77, wherein the enantiomer is R-DOTMA.
83. The method of clause 76 or clause 77, wherein the enantiomer is S-DOTMA.
84. The method of clause 76 or clause 77, wherein the enantiomer is R-DOEPC or S-DOEPC.
85. The method of clause 76 or clause 77, wherein the enantiomer is R-DOEPC.
86. The method of clause 76 or clause 77, wherein the enantiomer is S-DOEPC.
87. The method of any one of clauses 59 to 86, wherein the therapeutic factor is selected from the group consisting of interleukins 1-18, stem cell factor, basic FGF, EGF, G-CSF, GM-CSF, FLK-2 ligand, HILDA, MIP- 1α, TGF-β TGF-α, M-CSF, IFN-γ, IFN-α, IFN-β, soluble CD23, LIF, and combinations thereof.

88. The method of any one of clauses 59 to 86, wherein the therapeutic factor is a cytokine.

89. The method of clause 88, wherein the cytokine is GM-CSF.

90. The method of any one of clauses 59 to 86, wherein the therapeutic factor is an immune cell growth factor.

91. The method of any one of clauses 59 to 90, wherein the composition further comprises one or more antigens.

92. The method of clause 91, wherein one or more antigens is a protein-based antigen.

93. The method of clause 91, wherein one or more antigens is a peptide-based antigen.

94. The method of any one of clauses 91 to 93, wherein one or more antigens is selected from the group consisting of a cancer antigen, a viral antigen, a bacterial antigen, and a pathogenic antigen.

95. The method of any one of clauses 91 to 93, wherein one or more antigens is a cancer antigen.

96. The method of any one of clauses 91 to 93, wherein one or more antigens is a viral antigen.

97. The method of any one of clauses 91 to 93, wherein one or more antigens is a bacterial antigen.

98. The method of any one of clauses 91 to 93, wherein one or more antigens is a pathogenic antigen.

99. The method of clause 98, wherein the pathogenic antigen is a synthetic or recombinant antigen.

100. The method of any one of clauses 91 to 99, wherein at least one antigen is an HPV protein or peptide.

101. The method of any one of clauses 91 to 100, wherein at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQ-PETT (SEQ. ID. NO: 5), MHGDTPTLHEYMLDLQ-PETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13).

102. The method of any one of clauses 91 to 100, wherein at least one antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

103. The method of any one of clauses 91 to 100, wherein the antigens comprise one or more of the gp100 sequence (KVPRNQDWL [SEQ. ID. No. 8]) and the TRP2 sequence (SYVDFFVWL [SEQ. ID. No. 9]).

104. The method of any one of clauses 91 to 100, wherein the antigen comprises the sequence RAHYNIVTF (SEQ. ID. NO: 1).

105. The method of any one of clauses 91 to 100, wherein the antigen comprises the sequence GQAE-PDRAHYNIVTF (SEQ. ID. NO: 2).

106. The method of any one of clauses 91 to 100, wherein the antigen comprises the sequence KSSGQAE-PDRAHYNIVTF (SEQ. ID. NO: 3).

107. The method of any one of clauses 91 to 100, wherein the antigen comprises the sequence YMLDLQPETT (SEQ. ID. NO: 4).

108. The method of any one of clauses 91 to 100, wherein the antigen comprises the sequence KSSYMLDLQ-PETT (SEQ. ID. NO: 5).

109. The method of any one of clauses 91 to 100, wherein the antigen comprises the sequence MHGDTPTL-HEYMLDLQPETT (SEQ. ID. NO: 6).

110. The method of any one of clauses 91 to 100, wherein the antigen comprises the sequence LLMGTL-GIVCPICSQKP (SEQ. ID. NO: 7).

111. The method of any one of clauses 91 to 100, wherein the antigen comprises the sequence KVPRNQDWL (SEQ. ID. NO: 8).

112. The method of any one of clauses 91 to 100, wherein the antigen comprises the sequence SYVDFFVWL (SEQ. ID. NO: 9).

113. The method of any one of clauses 91 to 100, wherein the antigen comprises the sequence KYICNSSCM (SEQ. ID. NO: 10).

114. The method of any one of clauses 91 to 100, wherein the antigen comprises the sequence KSSKVPRNQDWL (SEQ. ID. NO: 11).

115. The method of any one of clauses 91 to 114, wherein at least one antigen is selected from the group consisting of a lipoprotein, a lipopeptide, and a protein or peptide modified with an amino acid sequence having an increased hydrophobicity or a decreased hydrophobicity.

116. The method of any one of clauses 91 to 115, wherein one or more antigens is a lipidated antigen or an antigen modified to increase hydrophobicity of the antigen.

117. The method of any one of clauses 91 to 116, wherein at least one antigen is a modified protein or peptide.

118. The method of clause 117, wherein the modified protein or peptide is bonded to a hydrophobic group.

119. The method of clause 118, wherein the modified protein or peptide bonded to a hydrophobic group further comprises a linker sequence between the antigen and the hydrophobic group.

120. The method of clause 118 or 119, wherein the hydrophobic group is a palmitoyl group.

121. The method of any one of clauses 91 to 120, wherein at least one antigen is an unmodified protein or peptide.

122. The method of any one of clauses 59 to 121, wherein the administration activates an immune response via the MAP kinase signaling pathway in cells of the immune system of the mammal.

123. The method of clause 122, wherein the MAP kinase signaling pathway is activated by stimulating at least one of ERK-1, ERK-2, and p38.

124. The method of clause 122 or clause 123, wherein the immune response activates cytotoxic T lymphocytes in the mammal.

125. The method of clause 124, wherein the cytotoxic T lymphocytes are CD8+ T cells.

126. The method of any one of clauses 122 to 125, wherein the immune response activates an antibody response in the mammal.

127. The method of any one of clauses 122 to 126, wherein the immune response activates interferon-gamma (IFN-γ) in the mammal.

128. The method of any one of clauses 59 to 127, wherein the administration enhances functional antigen-specific CD8+ T lymphocyte response.

129. A method of augmenting an immune response in a mammal, said method comprising the step of administering an effective amount of a vaccine composition to the mammal, wherein the vaccine composition comprises an adjuvant and a therapeutic factor.
130. The method of clause 129, wherein the reduction results in an increase in T-cell response in the mammal.
131. The method of clause 130, wherein the T-cell is a tumor-infiltrated T-cell.
132. The method of clause 130 or clause 131, wherein the T-cell response is a CD4+ T-cell response.
133. The method of clause 132, wherein the CD4+ T-cell is a tumor-infiltrated CD4+ T-cell.
134. The method of any one of clauses 129 to 133, wherein the T-cell response is a CD8+ T-cell response.
135. The method of clause 134, wherein the CD8+ T-cell is a tumor-infiltrated CD8+ T-cell.
136. The method of any one of clauses 129 to 135, wherein the mammal is a human.
137. The method of any one of clauses 129 to 136, wherein the adjuvant is an immunomodulator.
138. The method of any one of clauses 129 to 137, wherein the adjuvant is a cationic lipid.
139. The method of clause 138, wherein the cationic lipid is purified.
140. The method of clause 138 or clause 139, wherein the cationic lipid is selected from the group consisting of DOTAP, DOTMA, DOEPC, and combinations thereof.
141. The method of any one of clauses 138 to 140, wherein the cationic lipid is DOTAP.
142. The method of any one of clauses 138 to 140, wherein the cationic lipid is DOTMA.
143. The method of any one of clauses 138 to 140, wherein the cationic lipid is DOEPC.
144. The method of any one of clauses 129 to 137, wherein the adjuvant is an enantiomer of a cationic lipid.
145. The method of clause 144, wherein the enantiomer is purified.
146. The method of clause 144 or clause 145, wherein the enantiomer is R-DOTAP or S-DOTAP.
147. The method of clause 144 or clause 145, wherein the enantiomer is R-DOTAP.
148. The method of clause 144 or clause 145, wherein the enantiomer is S-DOTAP.
149. The method of clause 144 or clause 145, wherein the enantiomer is R-DOTMA or S-DOTMA.
150. The method of clause 144 or clause 145, wherein the enantiomer is R-DOTMA.
151. The method of clause 144 or clause 145, wherein the enantiomer is S-DOTMA.
152. The method of clause 144 or clause 145, wherein the enantiomer is R-DOEPC or S-DOEPC.
153. The method of clause 144 or clause 145, wherein the enantiomer is R-DOEPC.
154. The method of clause 144 or clause 145, wherein the enantiomer is S-DOEPC.
155. The method of any one of clauses 129 to 154, wherein the therapeutic factor is selected from the group consisting of interleukins 1-18, stem cell factor, basic FGF, EGF, G-CSF, GM-CSF, FLK-2 ligand, HILDA, MIP-1α, TGF-β, TGF-α, M-CSF, IFN-γ, 1FN-α, IFN-β, soluble CD23, LIF, and combinations thereof.
156. The method of any one of clauses 129 to 154, wherein the therapeutic factor is a cytokine.
157. The method of clause 156, wherein the cytokine is GM-CSF.
158. The method of any one of clauses 129 to 154, wherein the therapeutic factor is an immune cell growth factor.
159. The method of any one of clauses 129 to 158, wherein the composition further comprises one or more antigens.
160. The method of clause 159, wherein one or more antigens is a protein-based antigen.
161. The method of clause 159, wherein one or more antigens is a peptide-based antigen.
162. The method of any one of clauses 159 to 161, wherein one or more antigens is selected from the group consisting of a cancer antigen, a viral antigen, a bacterial antigen, and a pathogenic antigen.
163. The method of any one of clauses 159 to 161, wherein one or more antigens is a cancer antigen.
164. The method of any one of clauses 159 to 161, wherein one or more antigens is a viral antigen.
165. The method of any one of clauses 159 to 161, wherein one or more antigens is a bacterial antigen.
166. The method of any one of clauses 159 to 161, wherein one or more antigens is a pathogenic antigen.
167. The method of clause 166, wherein the pathogenic antigen is a synthetic or recombinant antigen.
168. The method of any one of clauses 159 to 167, wherein at least one antigen is an HPV protein or peptide.
169. The method of any one of clauses 159 to 168, wherein at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13).
170. The method of any one of clauses 159 to 168, wherein at least one antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.
171. The method of any one of clauses 159 to 168, wherein the antigens comprise one or more of the gp100 sequence (KVPRNQDWL [SEQ. ID. No. 8]) and the TRP2 sequence (SYVDFFVWL [SEQ. ID. No. 9]).
172. The method of any one of clauses 159 to 168, wherein the antigen comprises the sequence RAHYNIVTF (SEQ. ID. NO: 1).
173. The method of any one of clauses 159 to 168, wherein the antigen comprises the sequence GQAEPDRAHYNIVTF (SEQ. ID. NO: 2).
174. The method of any one of clauses 159 to 168, wherein the antigen comprises the sequence KSSGQAEPDRAHYNIVTF (SEQ. ID. NO: 3).
175. The method of any one of clauses 159 to 168, wherein the antigen comprises the sequence YMLDLQPETT (SEQ. ID. NO: 4).

176. The method of any one of clauses 159 to 168, wherein the antigen comprises the sequence KSSYMLDLQPETT (SEQ. ID. NO: 5).
177. The method of any one of clauses 159 to 168, wherein the antigen comprises the sequence MHGDTPTLHEYMLDLQPETT (SEQ. ID. NO: 6).
178. The method of any one of clauses 159 to 168, wherein the antigen comprises the sequence LLMGTLGIVCPICSQKP (SEQ. ID. NO: 7).
179. The method of any one of clauses 159 to 168, wherein the antigen comprises the sequence KVPRNQDWL (SEQ. ID. NO: 8).
180. The method of any one of clauses 159 to 168, wherein the antigen comprises the sequence SYVDFFVWL (SEQ. ID. NO: 9).
181. The method of any one of clauses 159 to 168, wherein the antigen comprises the sequence KYICNSSCM (SEQ. ID. NO: 10).
182. The method of any one of clauses 159 to 168, wherein the antigen comprises the sequence KSSKVPRNQDWL (SEQ. ID. NO: 11).
183. The method of any one of clauses 159 to 182, wherein at least one antigen is selected from the group consisting of a lipoprotein, a lipopeptide, and a protein or peptide modified with an amino acid sequence having an increased hydrophobicity or a decreased hydrophobicity.
184. The method of any one of clauses 159 to 183, wherein one or more antigens is a lipidated antigen or an antigen modified to increase hydrophobicity of the antigen.
185. The method of any one of clauses 159 to 184, wherein at least one antigen is a modified protein or peptide.
186. The method of clause 185, wherein the modified protein or peptide is bonded to a hydrophobic group.
187. The method of clause 185, wherein the modified protein or peptide bonded to a hydrophobic group further comprises a linker sequence between the antigen and the hydrophobic group.
188. The method of clause 186 or 187, wherein the hydrophobic group is a palmitoyl group.
189. The method of any one of clauses 159 to 188, wherein at least one antigen is an unmodified protein or peptide.
190. The method of any one of clauses 129 to 189, wherein the administration activates an immune response via the MAP kinase signaling pathway in cells of the immune system of the mammal.
191. The method of clause 190, wherein the MAP kinase signaling pathway is activated by stimulating at least one of ERK-1, ERK-2, and p38.
192. The method of clause 190 or clause 191, wherein the immune response activates cytotoxic T lymphocytes in the mammal.
193. The method of clause 192, wherein the cytotoxic T lymphocytes are CD8+ T cells.
194. The method of any one of clauses 190 to 193, wherein the immune response activates an antibody response in the mammal.
195. The method of any one of clauses 190 to 194, wherein the immune response activates interferon-gamma (IFN-γ) in the mammal.
196. The method of any one of clauses 129 to 195, wherein the administration enhances functional antigen-specific CD8+ T lymphocyte response.
197. A method of treating a disease in a mammal, said method comprising the step of administering an effective amount of a vaccine composition to the mammal, wherein the vaccine composition comprises an adjuvant and a therapeutic factor.
198. The method of clause 197, wherein the method is a prophylactic treatment.
199. The method of clause 197 or clause 198, wherein the disease is a cancer.
200. The method of any one of clauses 197 to 199, wherein the adjuvant is an immunomodulator.
201. The method of any one of clauses 197 to 200, wherein the adjuvant is a cationic lipid.
202. The method of clause 201, wherein the cationic lipid is purified.
203. The method of clause 201 or clause 202, wherein the cationic lipid is selected from the group consisting of DOTAP, DOTMA, DOEPC, and combinations thereof.
204. The method of any one of clauses 201 to 203, wherein the cationic lipid is DOTAP.
205. The method of any one of clauses 201 to 203, wherein the cationic lipid is DOTMA.
206. The method of any one of clauses 201 to 203, wherein the cationic lipid is DOEPC.
207. The method of any one of clauses 197 to 200, wherein the adjuvant is an enantiomer of a cationic lipid.
208. The method of clause 207, wherein the enantiomer is purified.
209. The method of clause 207 or clause 208, wherein the enantiomer is R-DOTAP or S-DOTAP.
210. The method of clause 207 or clause 208, wherein the enantiomer is R-DOTAP.
211. The method of clause 207 or clause 208, wherein the enantiomer is S-DOTAP.
212. The method of clause 207 or clause 208, wherein the enantiomer is R-DOTMA or S-DOTMA.
213. The method of clause 207 or clause 208, wherein the enantiomer is R-DOTMA.
214. The method of clause 207 or clause 208, wherein the enantiomer is S-DOTMA.
215. The method of clause 207 or clause 208, wherein the enantiomer is R-DOEPC or S-DOEPC.
216. The method of clause 207 or clause 208, wherein the enantiomer is R-DOEPC.
217. The method of clause 207 or clause 208, wherein the enantiomer is S-DOEPC.
218. The method of any one of clauses 197 to 217, wherein the therapeutic factor is selected from the group consisting of interleukins 1-18, stem cell factor, basic FGF, EGF, G-CSF, GM-CSF, FLK-2 ligand, HILDA, MIP-1α, TGF-β, TGF-α, M-CSF, IFN-α, IFN-β, soluble CD23, LIF, and combinations thereof.
219. The method of any one of clauses 197 to 217, wherein the therapeutic factor is a cytokine.
220. The method of clause 156, wherein the cytokine is GM-CSF.
221. The method of any one of clauses 197 to 217, wherein the therapeutic factor is an immune cell growth factor.
222. The method of any one of clauses 197 to 221, wherein the composition further comprises one or more antigens.
223. The method of clause 222, wherein one or more antigens is a protein-based antigen.
224. The method of clause 222, wherein one or more antigens is a peptide-based antigen.

225. The method of any one of clauses 222 to 224, wherein one or more antigens is selected from the group consisting of a cancer antigen, a viral antigen, a bacterial antigen, and a pathogenic antigen.
226. The method of any one of clauses 222 to 224, wherein one or more antigens is a cancer antigen.
227. The method of any one of clauses 222 to 224, wherein one or more antigens is a viral antigen.
228. The method of any one of clauses 222 to 224, wherein one or more antigens is a bacterial antigen.
229. The method of any one of clauses 222 to 224, wherein one or more antigens is a pathogenic antigen.
230. The method of clause 166, wherein the pathogenic antigen is a synthetic or recombinant antigen.
231. The method of any one of clauses 222 to 230, wherein at least one antigen is an HPV protein or peptide.
232. The method of any one of clauses 222 to 231, wherein at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13).
233. The method of any one of clauses 222 to 231, wherein at least one antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.
234. The method of any one of clauses 222 to 231, wherein the antigens comprise one or more of the gp100 sequence (KVPRNQDWL [SEQ. ID. No. 8]) and the TRP2 sequence (SYVDFFVWL [SEQ. ID. No. 9]).
235. The method of any one of clauses 222 to 231, wherein the antigen comprises the sequence RAHYNIVTF (SEQ. ID. NO: 1).
236. The method of any one of clauses 222 to 231, wherein the antigen comprises the sequence GQAEPDRAHYNIVTF (SEQ. ID. NO: 2).
237. The method of any one of clauses 222 to 231, wherein the antigen comprises the sequence KSSGQAEPDRAHYNIVTF (SEQ. ID. NO: 3).
238. The method of any one of clauses 222 to 231, wherein the antigen comprises the sequence YMLDLQPETT (SEQ. ID. NO: 4).
239. The method of any one of clauses 222 to 231, wherein the antigen comprises the sequence KSSYMLDLQPETT (SEQ. ID. NO: 5).
240. The method of any one of clauses 222 to 231, wherein the antigen comprises the sequence MHGDTPTLHEYMLDLQPETT (SEQ. ID. NO: 6).
241. The method of any one of clauses 222 to 231, wherein the antigen comprises the sequence LLMGTLGIVCPICSQKP (SEQ. ID. NO: 7).
242. The method of any one of clauses 222 to 231, wherein the antigen comprises the sequence KVPRNQDWL (SEQ. ID. NO: 8).
243. The method of any one of clauses 222 to 231, wherein the antigen comprises the sequence SYVDFFVWL (SEQ. ID. NO: 9).
244. The method of any one of clauses 222 to 231, wherein the antigen comprises the sequence KYICNSSCM (SEQ. ID. NO: 10).
245. The method of any one of clauses 222 to 231, wherein the antigen comprises the sequence KSSKVPRNQDWL (SEQ. ID. NO: 11).
246. The method of any one of clauses 222 to 231, wherein at least one antigen is selected from the group consisting of a lipoprotein, a lipopeptide, and a protein or peptide modified with an amino acid sequence having an increased hydrophobicity or a decreased hydrophobicity.
247. The method of any one of clauses 222 to 246, wherein one or more antigens is a lipidated antigen or an antigen modified to increase hydrophobicity of the antigen.
248. The method of any one of clauses 222 to 247, wherein at least one antigen is a modified protein or peptide.
249. The method of clause 248, wherein the modified protein or peptide is bonded to a hydrophobic group.
250. The method of clause 248, wherein the modified protein or peptide bonded to a hydrophobic group further comprises a linker sequence between the antigen and the hydrophobic group.
251. The method of clause 249 or 250, wherein the hydrophobic group is a palmitoyl group.
252. The method of any one of clauses 222 to 251, wherein at least one antigen is an unmodified protein or peptide.
253. The method of any one of clauses 197 to 252, wherein the administration activates an immune response via the MAP kinase signaling pathway in cells of the immune system of the mammal.
254. The method of clause 253, wherein the MAP kinase signaling pathway is activated by stimulating at least one of ERK-1, ERK-2, and p38.
255. The method of clause 253 or clause 254, wherein the immune response activates cytotoxic T lymphocytes in the mammal.
256. The method of clause 255, wherein the cytotoxic T lymphocytes are CD8+ T cells.
257. The method of any one of clauses 253 to 256, wherein the immune response activates an antibody response in the mammal.
258. The method of any one of clauses 253 to 257, wherein the immune response activates interferon-gamma (IFN-γ) in the mammal.
259. The method of any one of clauses 197 to 258, wherein the administration enhances functional antigen-specific CD8+ T lymphocyte response.
260. The vaccine composition of any one of clauses 24 to 34 or clauses 48 to 58, wherein the antigen comprises the sequence KSSMHGDTPTLHEYMLDLQPETT (SEQ. ID. NO: 12).
261. The vaccine composition of any one of clauses 24 to 34 or clauses 48 to 58, wherein the antigen comprises the sequence KSSLLMGTLGIVCPICSQKP (SEQ. ID. NO: 13).
262. The method of any one of clauses 91 to 100 or clauses 115 to 128, wherein the antigen comprises the sequence KSSMHGDTPTLHEYMLDLQPETT (SEQ. ID. NO: 12).

263. The method of any one of clauses 91 to 100 or clauses 115 to 128, wherein the antigen comprises the sequence KSSLLMGTLGIVCPICSQKP (SEQ. ID. NO: 13).

264. The method of any one of clauses 159 to 168 or clauses 183 to 196, wherein the antigen comprises the sequence KSSMHGDTPTLHEYMLDLQPETT (SEQ. ID. NO: 12).

265. The method of any one of clauses 159 to 168 or clauses 183 to 196, wherein the antigen comprises the sequence KSSLLMGTLGIVCPICSQKP (SEQ. ID. NO: 13).

266. The method of any one of clauses 222 to 231 or clauses 246 to 259, wherein the antigen comprises the sequence KSSMHGDTPTLHEYMLDLQPETT (SEQ. ID. NO: 12).

267. The method of any one of clauses 222 to 231 or clauses 246 to 259, wherein the antigen comprises the sequence KSSLLMGTLGIVCPICSQKP (SEQ. ID. NO: 13).

Figure 1:
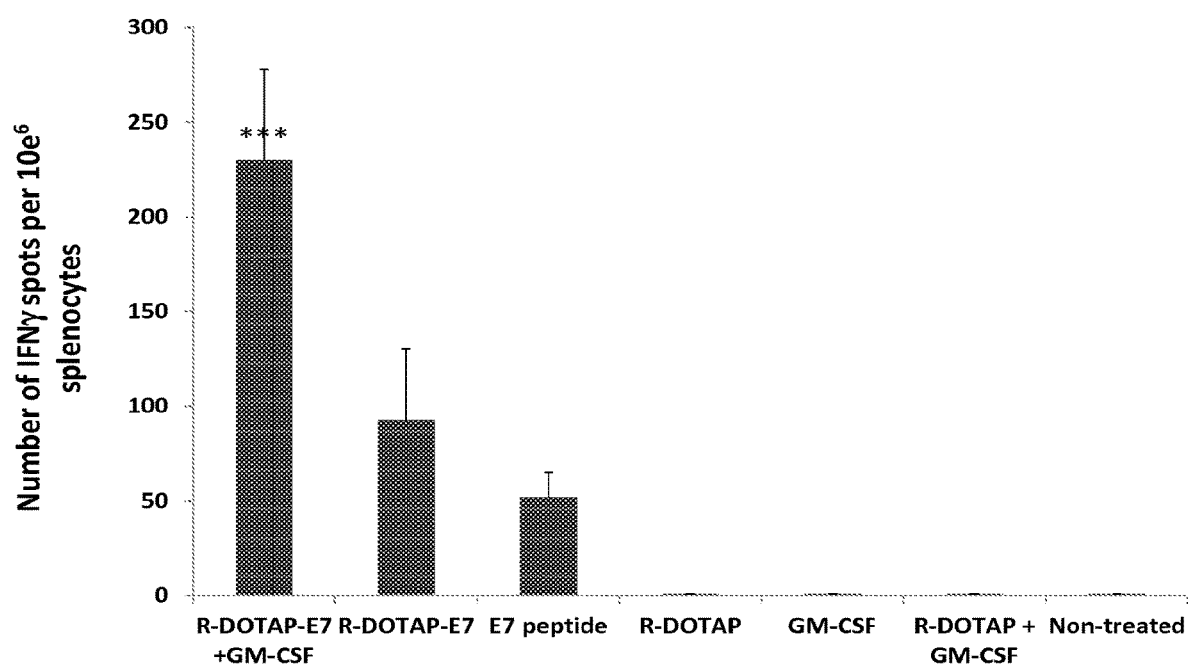
FIG. 1 shows the effect of various vaccine compositions on the antigen-specific immune response in tumor-bearing mice. The number of IFN-ã spots observed per $10^6$ splenocytes from mice are presented as number of spots from $E7_{49\_57}$ re-stimulated culture minus control antigen re-stimulated culture per million splenocytes±SD. E7 peptide in the figure refers to GM-CSF-E7+Cd40+IFA. (***P<0.001).

Various embodiments of the invention are described herein as follows. In one embodiment described herein, a vaccine composition is provided. The vaccine composition comprises an adjuvant and a therapeutic factor.

In another embodiment, a method of reducing an immune suppressor cell population in a mammal is provided. The method comprises the step of administering an effective amount of a vaccine composition to the mammal, wherein the vaccine composition comprises an adjuvant and a therapeutic factor.

In yet another embodiment, a method of augmenting an immune response in a mammal is provided. The method comprises the step of administering an effective amount of a vaccine composition to the mammal, wherein the vaccine composition comprises an adjuvant and a therapeutic factor.

In yet another embodiment, a method of treating a disease in a mammal is provided. The method comprises the step of administering an effective amount of a vaccine composition to the mammal, wherein the vaccine composition comprises an adjuvant and a therapeutic factor.

In the various embodiments, the vaccine composition comprises an adjuvant and a therapeutic factor. As used herein, the term "adjuvant" refers to a substance that enhances, augments and/or potentiates a mammal's immune response to an antigen. As used herein, the term "therapeutic factor" refers to any agent associated with the treatment of disease by inducing, enhancing, or suppressing an immune response. As used herein, a therapeutic factor includes but is not limited to an immune system stimulant, a cell killing agent, a tumor penetration enhancer, a chemotherapeutic agent, or a cytotoxic immune cell. It is contemplated that the vaccine composition includes formulations in which the adjuvant and the therapeutic factor are administered together, as well as formulations in which the adjuvant and the therapeutic factor are administered separately. Doses of the adjuvant and the therapeutic factor are known to those of ordinary skill in the art.

In some embodiments described herein, the adjuvant is an immunomodulator. As used herein, the term "immunomodulator" refers to an immunologic modifier that enhances, directs, and/or promotes an immune response in a mammal.

In some embodiments described herein, the adjuvant is a nanoparticle. As used herein, the term "nanoparticle" refers to a particle having a size measured on the nanometer scale. As used herein, the "nanoparticle" refers to a particle having a structure with a size of less than about 1,000 nanometers. In some embodiments, the nanoparticle is a liposome.

In some embodiments described herein, the adjuvant is a cationic lipid. As used herein, the term "cationic lipid" refers to any of a number of lipid species which carry a net positive charge at physiological pH or have a protonatable group and are positively charged at pH lower than the pKa.

Suitable cationic lipid according to the present disclosure include, but are not limited to: 3-.beta.r.sup.4N-(.sup.1N,.sup.8-diguanidino spermidine)-carbamoyl]cholesterol (BGSC); 3-.beta. [N,N-diguanidinoethyl-aminoethane)-carbamoyl] cholesterol (BGTC); N,N.sup.1N.sup.2N.sup.3Tetra-methyltetrapalmityl spermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2(sperminecarboxamido)ethyl]-N,N-dimethyl-1-propanaminium trifluorocetate) (DOSPA); 1,3-dioleoyloxy-2-(6-carboxyspermyl)-propyl amide (DOSPER); 4-(2,3-bi s-palmitoyloxy-propyl)-1-methyl-1H-imidazole (DPIM) N,N,N',N'-tetramethyl-N,N'-bis(2-hydroxyethyl)-2,3-dioleoyloxy-1,4-butane-diammonium iodide) (Tfx-50); N-1-(2,3-dioleoyloxy) propyl-N,N,N-trimethyl ammonium chloride (DOTMA) or other N-(N,N-1-dialkoxy)-alkyl-N,N,N-tri substituted ammonium surfactants; 1,2 dioleoyl-3-(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DORI (DL-1,2-dioleoyl-3-dimethylaminopropyl-.beta.-hydroxyethylammonium) or DOME (DL-1,2-0-dioleoyl-3-dimethylaminopropyl-.beta.-hydroxyethylammonium) (DORIE) or analogs thereof as disclosed in WO 93/03709; 1,2-dioleoyl- 3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES), cholesteryl-3.beta.-carboxyl-amido-ethylenetrimethylammonium iodide, 1-dimethylamino-3-trimethylammonio-DL-2-propyl-cholesteryl carboxylate iodide, cholesteryl-3-0-carboxyamidoethyleneamine, cholesteryl-3-.beta.-oxysuccinamido-ethylenetrimethylammonium iodide, 1-dimethylamino-3-trimethylammonio-DL-2-propyl-cholesteryl-3-.beta.-oxysuccinateiodide, 2-(2-trimethylammonio)-ethylmethylaminoethyl-cholesteryl-3-.beta.-oxysuccinate iodide, 3-.beta.-N-(N',N'-dimethylaminoethane) carbamoyl cholesterol (DC-chol), and 3-.beta.-N-(polyethyleneimine)-carbamoylcholesterol; 0,0'-dimyristyl-N-lysyl aspartate (DMKE); O,O'-dimyrityl-N-lysyl-glutamate (DMKD); 1,2-dimyristyloxypropyl-3-dimethyl-hydroxy ethyl ammonium bromide (DMRIE); 1,2-dilauroyl-sn-glycero-3-ethylphosphocholine (DLEPC); 1,2-dimyristoyl-sn-glycero-3-ethylphosphocholine (DMEPC); 1,2-dioleoyl-sn-glycero-3-ethylphosphocholine (DOEPC); 1,2-dipalmitoyl-sn-glycero-3-ethylphosphocholine (DPEPC); 1,2-di stearoyl-sn-glycero-3-ethylphosphocholine (DSEPC); 1,2-dioleoyl-3-trimethylammonium propane (DOTAP); dioleoyl dimethylaminopropane (DODAP); 1,2-palmitoyl-3-trimethylammonium propane (DPTAP); 1,2-distearoyl-3-trimethylammonium propane (DSTAP), 1,2-myristoyl-3-trimethylammonium propane (DMTAP); and sodium dodecyl sulfate (SDS). Furthermore, structural variants and derivatives of the any of the described cationic lipids are also contemplated.

In some embodiment, the cationic lipid is selected from the group consisting of DOTAP, DOTMA, DOEPC, and combinations thereof. In other embodiments, the cationic lipid is DOTAP. In yet other embodiments, the cationic lipid is DOTMA. In other embodiments, the cationic lipid is DOEPC. In some embodiments, the cationic lipid is purified.

In some embodiments, the cationic lipid is an enantiomer of a cationic lipid. The term "enantiomer" refers to a stereoisomer of a cationic lipid which is a non-superimposable mirror image of its counterpart stereoisomer, for example R and S enantiomers. In various examples, the enantiomer is R-DOTAP or S-DOTAP. In one example, the enantiomer is R-DOTAP. In another example, the enantiomer is S-DOTAP. In some embodiments, the enantiomer is purified. In various examples, the enantiomer is R-DOTMA or S-DOTMA. In 20 one example, the enantiomer is R-DOTMA. In another example, the enantiomer is S-DOTMA. In some embodiments, the enantiomer is purified. In various examples, the enantiomer is R-DOPEC or S-DOPEC. In one example, the enantiomer is R-DOPEC. In another example, the enantiomer is S-DOPEC. In some embodiments, the enantiomer is purified.

In various embodiments described herein, the therapeutic factor is selected from the group consisting of interleukins 1-18, stem cell factor, basic FGF, EGF, G-CSF, GM-CSF, FLK-2 ligand, HILDA, MIP-1α, TGF-β, TGF-α, M-CSF, IFN-γ, IFN-α, IFN-β, soluble CD23, LIF, and combinations thereof. Other therapeutic factors are known to those of ordinary skill in the art and may also be used in the vaccine compositions of the present disclosure.

In various embodiments described herein, the therapeutic factor is a cytokine. In some embodiments, the cytokine is GM-CSF. In other embodiments described herein, the therapeutic factor is an immune cell growth factor.

In various embodiments described herein, the composition further comprises one or more antigens. As used herein, the term "antigen" refers to any agent (e.g., protein, peptide, polysaccharide, glycoprotein, glycolipid, nucleic acid, or combination thereof) that, when introduced into a mammal having an immune system (directly or upon expression as in, e.g., DNA vaccines), is recognized by the immune system of the mammal and is capable of eliciting an immune response. As defined herein, the antigen-induced immune response can be humoral or cell-mediated, or both. An agent is termed "antigenic" when it is capable of specifically interacting with an antigen recognition molecule of the immune system, such as an immunoglobulin (antibody) or T cell antigen receptor (TCR).

In some embodiments, one or more antigens is a protein-based antigen. In other embodiments, one or more antigens is a peptide-based antigen. In various embodiments, one or more antigens is selected from the group consisting of a cancer antigen, a viral antigen, a bacterial antigen, and a pathogenic antigen. A "microbial antigen," as used herein, is an antigen of a microorganism and includes, but is not limited to, infectious virus, infectious bacteria, infectious parasites and infectious fungi. Microbial antigens may be intact microorganisms, and natural isolates, fragments, or derivatives thereof, synthetic compounds which are identical to or similar to naturally-occurring microbial antigens and, preferably, induce an immune response specific for the corresponding microorganism (from which the naturally-occurring microbial antigen originated). In one embodiment, the antigen is a cancer antigen. In one embodiment, the antigen is a viral antigen. In another embodiment, the antigen is a bacterial antigen. In various embodiments, the antigen is a pathogenic antigen. In some embodiments, the pathogenic antigen is a synthetic or recombinant antigen.

In some embodiments, the antigen is a cancer antigen. A "cancer antigen," as used herein, is a molecule or compound (e.g., a protein, peptide, polypeptide, lipoprotein, lipopeptide, glycoprotein, glycopeptides, lipid, glycolipid, carbohydrate, RNA, and/or DNA) associated with a tumor or cancer cell and which is capable of provoking an immune response (humoral and/or cellular) when expressed on the surface of an antigen presenting cell in the context of an MHC molecule. For example, a cancer antigen may be a tumor-associated antigen. Tumor-associated antigens include self antigens, as well as other antigens that may not be specifically associated with a cancer, but nonetheless enhance an immune response to and/or reduce the growth of a tumor or cancer cell when administered to a mammal. In one embodiment, at least one antigen is an HPV protein or peptide.

In some embodiments of the present disclosure, at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13). In one embodiment, at least one antigen comprises the sequence RAHYNIVTF (SEQ. ID. NO: 1). In another embodiment, at least one antigen comprises the sequence GQAEPDRAHYNIVTF (SEQ. ID. NO: 2). In yet another embodiment, at least one antigen comprises the sequence KSSGQAEPDRAHYNIVTF (SEQ. ID. NO: 3). In some embodiments, KSSGQAEPDRAHYNIVTF (SEQ. ID. NO: 3) is modified to further comprise a hydrophobic group. In one embodiment, the hydrophobic group is a palmitoyl group.

In other embodiments, at least one antigen comprises the sequence YMLDLQPETT (SEQ. ID. NO: 4). In another embodiment, at least one antigen comprises the sequence KSSYMLDLQPETT (SEQ. ID. NO: 5). In yet another embodiment, KSSYMLDLQPETT (SEQ. ID. NO: 5) is modified to further comprise a hydrophobic group. In one embodiment, the hydrophobic group is a palmitoyl group.

In other embodiments, at least one antigen comprises the sequence MHGDTPTLHEYMLDLQPETT (SEQ. ID. NO: 6). In another embodiment, MHGDTPTLHEYMLDLQPETT (SEQ. ID. NO: 6) is modified to further comprise a hydrophobic group. In one embodiment, the hydrophobic group is a palmitoyl group. In other embodiments, at least one antigen comprises the sequence LLMGTLGIVCPICSQKP (SEQ. ID. NO: 7). In some embodiments, LLMGTLGIVCPICSQKP (SEQ. ID. NO: 7) is modified to further comprise a hydrophobic group. In one embodiment, the hydrophobic group is a palmitoyl group.

In some embodiments, at least one antigen comprises the sequence KVPRNQDWL (SEQ. ID. NO: 8). In other embodiments, at least one antigen comprises the sequence SYVDFFVWL (SEQ. ID. NO: 9). In yet other embodiments, at least one antigen comprises the sequence KYICNSSCM (SEQ. ID. NO: 10). In another embodiment, at least one antigen comprises the sequence KSSKVPRNQDWL (SEQ. ID. NO: 11). In some embodiments, KSSKVPRNQDWL (SEQ. ID. NO: 11) is modified to further comprise a hydrophobic group. In one embodiment, the hydrophobic group is a palmitoyl group. In other embodiments, at least one antigen comprises the sequence KSSMHGDTPTLHEYMLDLQPETT (SEQ. ID. NO: 12). In another embodiment, KSSMHGDTPTLHEYMLDLQPETT (SEQ. ID. NO: 12) is modified to further comprise a hydrophobic group. In one embodiment, the hydrophobic group is a palmitoyl group.

In other embodiments, at least one antigen comprises the sequence KSSLLMGTLGIVCPICSQKP (SEQ. ID. NO: 13). In some embodiments, KSSLLMGTLGIVCPICSQKP (SEQ. ID. NO: 13) is modified to further comprise a hydrophobic group. In one embodiment, the hydrophobic group is a palmitoyl group.

In one embodiment, the antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

In one embodiment, the antigens comprise one or more of the gp100 sequence (KVPRNQDWL [SEQ. ID. No. 8]) and the TRP2 sequence (SYVDFFVWL [SEQ. ID. No. 9]). In various embodiments, at least one antigen is selected from the group consisting of a lipoprotein, a lipopeptide, and a protein or peptide modified with an amino acid sequence having an increased hydrophobicity or a decreased hydrophobicity. In some embodiments, one or more antigens is an antigen modified to increase hydrophobicity of the antigen. In one embodiment, at least one antigen is a modified protein or peptide. In some embodiments, the modified protein or peptide is bonded to a hydrophobic group. In other embodiments, the modified protein or peptide bonded to a hydrophobic group further comprises a linker sequence between the antigen and the hydrophobic group. In some embodiments, the hydrophobic group is a palmitoyl group. In yet other embodiments, at least one antigen is an unmodified protein or peptide.

In various embodiments described herein, the vaccine composition induces an immune response in a mammal by activating the mitogen-activated protein (MAP) kinase signaling pathway. Induction of an immune response by adjuvants such as cationic lipids are described, for example, in PCT/US2008/057678 (WO/2008/116078; "Stimulation of an Immune Response by Cationic Lipids") and PCT/US2009/040500 (WO/2009/129227; "Stimulation of an Immune Response by Enantiomers of Cationic Lipids"), the entire disclosures of both incorporated herein by reference. In some embodiments, the MAP kinase signaling pathway is activated by stimulating at least one of extracellular signal-regulated kinase ("ERK")-1, ERK-2, and p38. In other embodiments, the composition enhances functional antigen-specific CD8+ T lymphocyte response. The term "mammal" is well known to those of skill in the art. In one embodiment, the mammal is a human.

In one embodiment described herein, a method of reducing an immune suppressor cell population in a mammal is provided. The method comprises comprising the step of administering an effective amount of a vaccine composition to the mammal, wherein the vaccine composition comprises an adjuvant and a therapeutic factor. The previously described embodiments of the vaccine composition are applicable to the method of reducing an immune suppressor cell population in a mammal described herein.

In some embodiments, the immune suppressor cell is a myeloid-derived suppressor cell (MDSC). In other embodiments, the immune suppressor cell is a T regulatory cell.

In various embodiments, the reduction results in an increase in T-cell response in the mammal. In some embodiments, the T-cell is a tumor-infiltrated T-cell. In some embodiments, the T-cell response is a CD4+ T-cell response. In certain embodiments, the CD4+ T-cell is a tumor-infiltrated CD4+ T-cell. In some embodiments, the T-cell response is a CD8+ T-cell response. In certain embodiments, the CD8+ T-cell is a tumor-infiltrated CD8+ T-cell.

In various embodiments, the mammal is a human. In some embodiments, the administration activates an immune response via the MAP kinase signaling pathway in cells of the immune system of the mammal. In various embodiments, the MAP kinase signaling pathway is activated by stimulating at least one of ERK-1, ERK-2, and p38.

In other embodiments, the immune response activates cytotoxic T lymphocytes in the mammal. In one embodiment, the cytotoxic T lymphocytes are CD8+ T cells. In another embodiment, the administration enhances functional antigen-specific CD8+ T lymphocyte response. In yet another embodiment, the immune response activates an antibody response in the mammal. In other embodiments, the immune response activates interferon-gamma (IFN-α) in the mammal.

In one embodiment described herein, a method of augmenting an immune response in a mammal is provided. The method comprises the step of administering an effective amount of a vaccine composition to the mammal, wherein the vaccine composition comprises an adjuvant and a therapeutic factor. The previously described embodiments of the vaccine composition and of the method of reducing an immune suppressor cell population in a mammal are applicable to the method of augmenting an immune response in a mammal described herein.

In one embodiment described herein, a method of treating a disease in a mammal is provided. The method comprises the step of administering an effective amount of a vaccine composition to the mammal, wherein the vaccine composition comprises an adjuvant and a therapeutic factor. The previously described embodiments of the vaccine composition and of the method of reducing an immune suppressor cell population in a mammal are applicable to the method of treating a disease in a mammal described herein.

In some embodiments, "treatment," "treat," and "treating," as used herein with reference to infectious pathogens, refer to a prophylactic treatment which increases the resistance of a subject to infection with a pathogen or decreases the likelihood that the subject will become infected with the pathogen; and/or treatment after the subject has become infected in order to fight the infection, e.g., reduce or eliminate the infection or prevent it from becoming worse. In one embodiment, the method is a prophylactic treatment. In some embodiments, the disease is a cancer.

EXAMPLE 1

Preparation of Adjuvant and Adjuvants Incorporating an Antigen

Adjuvants may be prepared using cationic lipids alone. Alternatively, adjuvants may be prepared using mixtures of cationic lipids and other immunomodulators. Vaccine compositions may be prepared using a cationic lipid-based composition incorporating an antigen. In the present example, DOTAP was used as an exemplary cationic lipid and HPV protein E7 peptide antigen was used as an exemplary antigen.

Sterile water for injection (WFI) or a buffer was used in all procedures in which cationic lipids were prepared into liposomes. In this example, liposomes were prepared using lipid films. The E7 antigen used for incorporation into the liposomes was an H-2D$^b$ restricted CTL epitope (amino acid 49-57, RAHYNIVTF [SEQ. ID. NO. 1]) derived from HPV 16 E7 protein. Lipid films were made in glass vials by (1) dissolving the lipids in an organic solvent such as chloroform, and (2) evaporating the chloroform solution under a steady stream of dry nitrogen gas. Traces of organic solvent were removed by keeping the films under vacuum overnight. The lipid films were then hydrated by adding the required amount of WFI or buffer to make a final concentration of 4-10 mg/mL. The suspensions were then extruded to a size of 200 nm and stored at 4° C.

For the preparation of cationic lipid incorporating an antigen, the DOTAP lipid film was rehydrated by an aqueous solution of E7 peptide. Other methods used in general liposome preparation that are well known to those skilled in the art may also be used.

EXAMPLE 2

Effect of Vaccine Compositions on Antigen-Specific Immune Response in Tumor-Bearing Mice Various vaccine compositions may be compared according to the present disclosure and evaluated for their effects on antigen-specific immune response in tumor-bearing mice. In this example, R-DOTAP was used as an exemplary cationic lipid, E7 peptide was used as an exemplary antigen, and the cytokine GM-C SF was used as an exemplary therapeutic factor. Furthermore, anti-CD40 Ab and incomplete Freund's adjuvant (IFA) were used as comparative adjuvants.

In this example, vaccine compositions were prepared according to the disclosure and the following groups were evaluated:

Group 1: R-DOTAP-E7 peptide (20 jug/mouse) and GM-CSF (5 µg/mouse)
Group 2: R-DOTAP-E7 peptide (20 jug/mouse)
Group 3: GM-CSF (5 µg/mouse), E7 peptide (10 Oug/mouse), anti-CD40 Ab (20 µg/mouse), and IFA (50 µg/mouse)
Group 4: R-DOTAP alone
Group 5: GM-CSF alone
Group 6: R-DOTAP and GM-C SF
Group 7: Untreated control Female C57BL6 mice aged 6-8 weeks old (5 mice per group) were implanted with 50,000 TC-1 cells/mouse subcutaneously in the right flank on day 0. On day 8, when all mice had tumors of 3-4 mm in diameter, subjects from each group were with the vaccine composition of the appropriate group.

Treatment was repeated on day 15. Six days later (i.e., day 21 after tumor implantation), mice were sacrificed. The spleens of the mice were harvested and processed for total lymphocytes. IFNγ activity in the presence of E7$_{49-57}$ peptide vs. irrelevant peptide control (10 µg/ml each) was assayed by ELISPOT. The number of spots from E7$_{49-57}$ re-stimulated culture minus irrelevant antigen re-stimulated culture per million splenocytes was evaluated.

As shown in FIG. 1, Group 1 (i.e., R-DOTAP-E7 peptide and GM-CSF) exhibited a statistically significant increase in antigen-specific immune response in tumor bearing mice compared to the other groups. The combination of R-DOTAP-E7 peptide and GM-CSF exhibited a synergistic effect on antigen-specific immune response compared to the individual components. Group 3 (i.e., GM-CSF, E7 peptide, anti-CD40 Ab, and IFA) was administered growth factor and a non-cationic lipid adjuvant, but did not exhibit a synergistic effect on the immune response as observed with Group 1.

EXAMPLE 3

Effect of Vaccine Compositions on MDSC in the Tumor Micro-Environment of Tumor-Bearing Mice Various vaccine compositions may be compared according to the present disclosure and evaluated for their effects on MDSC number in the tumor micro-environment in tumor-bearing mice. In this example, R-DOTAP was used as an exemplary cationic lipid, E7 peptide was used as an exemplary antigen, and the cytokine GM-CSF was used as an exemplary therapeutic factor.

In this example, vaccine compositions were prepared according to the disclosure and the following groups were evaluated:

Group 1: R-DOTAP-E7 peptide (20 µg/mouse) and GM-CSF (5[(g/mouse)
Group 2: R-DOTAP-E7 peptide (20 µg/mouse)
Group 3: R-DOTAP alone
Group 4: GM-CSF alone
Group 5: R-DOTAP and GM-CSF
Group 6: Untreated control Female C57BL6 mice aged 6-8 weeks old (5 mice per group) were implanted with 50,000 TC-1 cells/mouse subcutaneously in the right flank on day 0. On day 8, when all mice had tumors of 3-4 mm in diameter, subjects from each group were with the vaccine composition of the appropriate group.

Treatment was repeated on day 15. Six days later (i.e., day 21 after tumor implantation), tumor tissue was harvested from the mice. Tumor samples were processed using GentleMACS Dissociator (Miltenyi Biotec, Auburn, CA) and the solid tumor homogenization protocol, as suggested by the manufacturer The number of tumor-infiltrated MDSC (defined as $CD11b^+Gr-1^-$ cells) was analyzed within the population of $CD44^+$ cells (marker for hematopoietic cells) using flow cytometry assay. The numbers of tumor-infiltrated cells were standardized per 1×106 of total tumor cells and presented as mean values.

Figure 2:
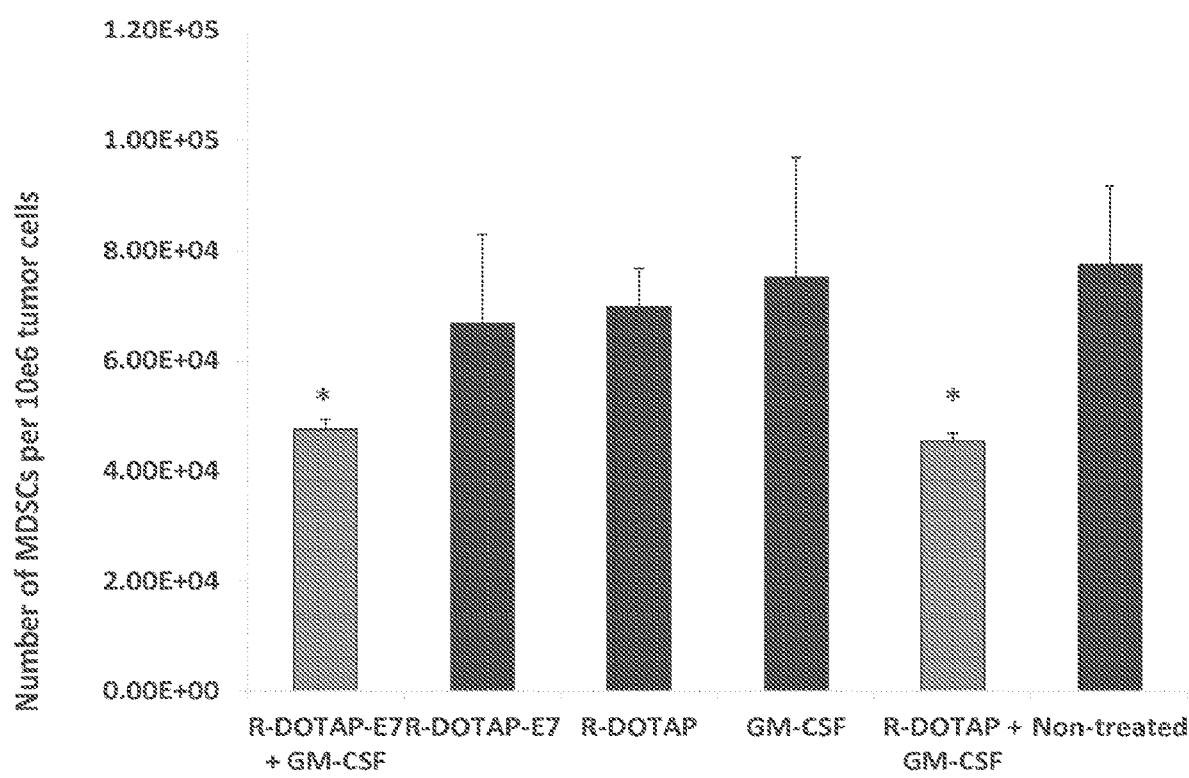
FIG. 2 shows the effect of various vaccine compositions on the number of tumor-infiltrated MDSC (defined as $CD11^+$ $Gr-1^+$ cells within the population of $CD44^+$ cells) using a flow cytometry assay. The numbers of tumor-infiltrated cells are standardized per $1\times10^6$ of total tumor cells and presented as mean values±SD. (*P<0.05 compared to the untreated and GM-CSF only groups).

As shown in FIG. 2, both Group 1 (i.e., R-DOTAP-E7 peptide and GM-CSF) and Group 5 (i.e., R-DOTAP-E7 and GM-CSF) exhibited a statistically significant decrease in MDSC number in tumor bearing mice compared to untreated mice and mice trated with GM-CSF only. The combination of R-DOTAP-E7 peptide and GM-C SF exhibited a synergistic effect to reduce the number of MDSC compared to the individual components. In addition, the combination of R-DOTAP and GM-CSF (i.e., without the administration of an antigen) exhibited a similar synergistic effect to reduce the number of MDSC compared to the individual components.

EXAMPLE 4

Effect of Vaccine Compositions on Tumor-Infiltrating CD8+ T-cells in Tumor-Bearing Mice Various vaccine compositions may be compared according to the present disclosure and evaluated for their effects on the number of tumor-infiltrating CD8+ T-cells in tumor-bearing mice. In this example, R-DOTAP was used as an exemplary cationic lipid, E7 peptide was used as an exemplary antigen, and the cytokine GM-C SF was used as an exemplary therapeutic factor.

In this example, vaccine compositions were prepared according to the disclosure and the following groups were evaluated:
Group 1: R-DOTAP-E7 peptide (20 µg/mouse) and GM-CSF (Slug/mouse)
Group 2: R-DOTAP-E7 peptide (20 µg/mouse)
Group 3: R-DOTAP alone
Group 4: GM-CSF alone
Group 5: R-DOTAP and GM-CSF
Group 6: Untreated control Female C57BL6 mice aged 6-8 weeks old (5 mice per group) were implanted with 50,000 TC-1 cells/mouse subcutaneously in the right flank on day 0. On day 8, when all mice had tumors of 3-4 mm in diameter, subjects from each group were with the vaccine composition of the appropriate group.

Treatment was repeated on day 15. Six days later (i.e., day 21 after tumor implantation), tumor tissue was harvested from the mice. Tumor samples were processed using GentleMACS Dissociator (Miltenyi Biotec, Auburn, CA) and the solid tumor homogenization protocol, as suggested by the manufacturer The number of tumor-infiltrated CD8+ T-Cells were analyzed within the population of $CD44^+$ cells (marker for hematopoietic cells) using flow cytometry assay. The numbers of tumor-infiltrated cells were standardized per 1×106 of total tumor cells and presented as mean values.

Figure 3:
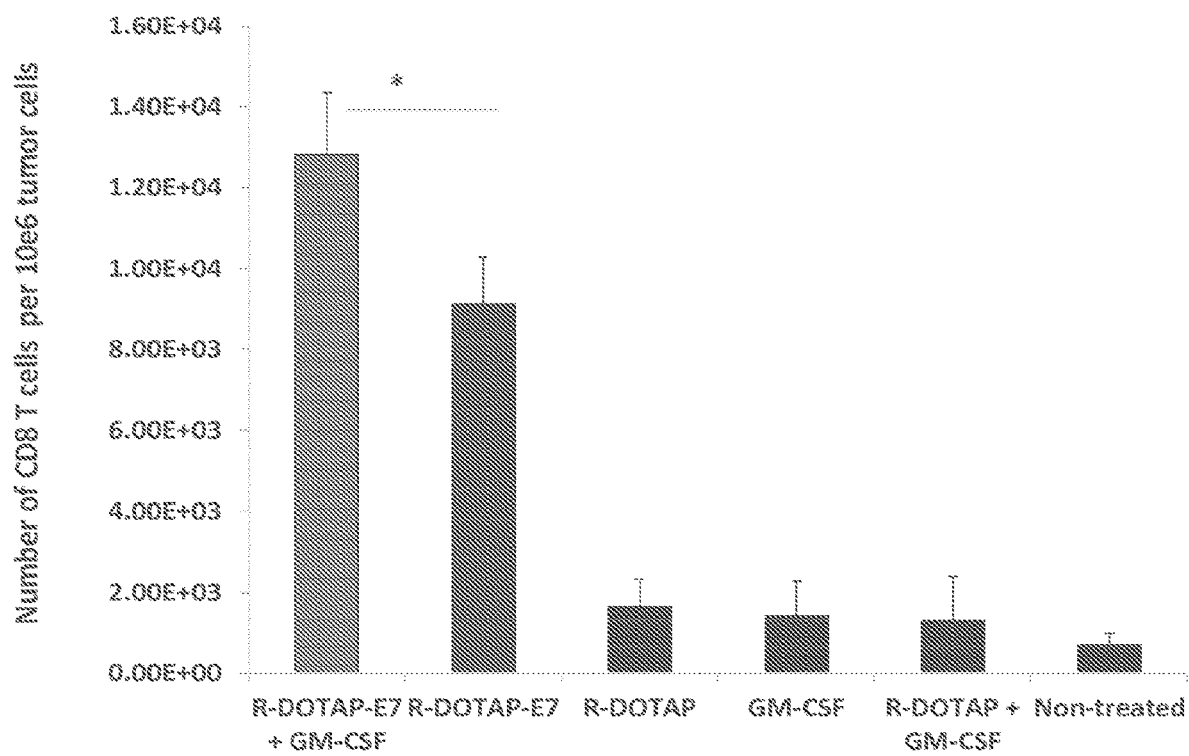
FIG. 3 shows the effect of various vaccine compositions on the number of tumor-infiltrating CD8+ T-cells following administration to mice. The number of tumor-infiltrated CD8+ T-Cells was analyzed within the population of $CD44^+$ cells using flow cytometry assay. The numbers of tumor-infiltrated cells were standardized per 1×106 of total tumor cells and are presented as mean values±SD. (*P<0.05).

As shown in FIG. 3, both Group 1 (i.e., R-DOTAP-E7 peptide and GM-CSF) and Group 2 (i.e., R-DOTAP-E7) exhibited a statistically significant increase in the number of tumor-infiltrated CD8+ T-Cells in tumor bearing mice compared to the other groups. The combination of R-DOTAP-E7 peptide and GM-C SF exhibited a synergistic effect to increase the number of tumor-infiltrated CD8+ T-Cells compared to the individual components.

EXAMPLE 5

Effect of Vaccine Compositions on Antigen-Specific Immune Response in Mice

Various vaccine compositions may be compared according to the present disclosure and evaluated for their effects on antigen-specific immune response in mice. In this example, R-DOTAP was used as an exemplary cationic lipid, TRP-2 and gp-100 peptides were used as an exemplary antigen, and the cytokine GM-C SF was used as an exemplary therapeutic factor.

In this example, vaccine compositions were prepared according to the disclosure and the following groups were evaluated:
Group 1: R-DOTAP/TRP-2/gp100 peptide (190 ug/160 ug)
Group 2: R-DOTAP/TRP-2/gp100 peptide/GM-C SF (190 ug/160 ug/0.5 ug)

Female C57BL6 mice aged 6-8 weeks old (4 mice per group) were used in the study. On days 0 and 8, subjects from each group were with the vaccine composition of the appropriate group.

Seven days later (i.e., day 14 after first administration), mice were sacrificed and their spleens were harvested and processed for total lymphocytes. IFNγ activity in the presence of TRP-2 and gp-100 peptides vs. irrelevant peptide control (10 µg/ml each) was assayed by ELISPOT. Values were presented as number of spots from TRP-2 and gp100 re-stimulated culture minus irrelevant antigen re-stimulated culture per million splenocytes.

Figure 4:
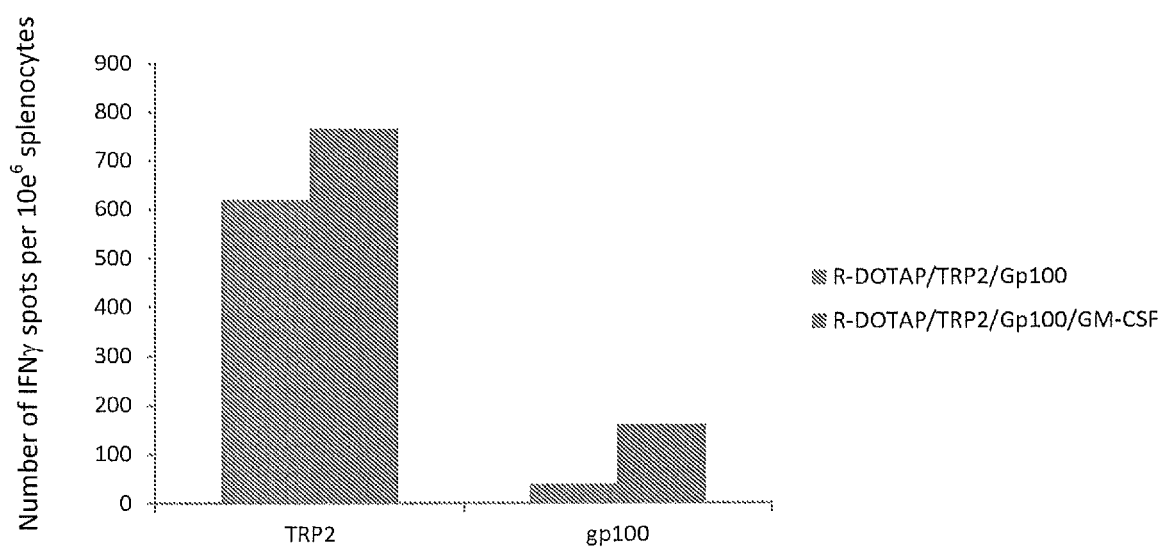
FIG. 4 shows the effect of various vaccine compositions on antigen-specific immune response. IFNα activity in the presence of the melanoma antigens TRP-2 and gp-100 peptides vs. peptide control (10 µg/ml each) was assayed by ELISPOT. Values are presented as number of spots from TRP-2 and gp100 re-stimulated culture minus control antigen re-stimulated culture per million splenocytes. (*P<0.01).

As shown in FIG. 4, Group 2 (i.e., R-DOTAP/TRP-2/gp100 peptide/GM-CSF) exhibited a statistically significant increase in antigen-specific immune response compared to Group 1, which did not include GM-CSF.

While the invention has been illustrated and described in detail in the foregoing description, such an illustration and description is to be considered as exemplary and not restrictive in character, it being understood that only the illustrative embodiments have been described and that all changes and modifications that come within the scope of the invention are desired to be protected. Those of ordinary skill in the art may readily devise their own implementations that incorporate one or more of the features described herein, and thus fall within the scope of the present disclosure.

What is claimed:

1. A method of reducing an immune suppressor cell population in a mammal, said method comprising the step of administering an effective amount of a composition to the mammal, wherein the composition comprises an adjuvant and a therapeutic factor, wherein the adjuvant is a cationic lipid and wherein the therapeutic factor is a cytokine selected from interleukins 1-18.

2. The method of claim 1, wherein the immune suppressor cell is a myeloid-derived suppressor cell (MDSC).

3. The method of claim 1, wherein the cationic lipid is selected from the group consisting of DOTAP, DOTMA, DOEPC, and combinations thereof.

4. The method of claim 1, wherein the cationic lipid is DOTAP.

5. The method of claim 1, wherein the adjuvant is an enantiomer of the cationic lipid.

6. The method of claim 5, wherein the enantiomer is R-DOTAP.

7. The method of claim 1, wherein the composition further comprises one or more antigens.

8. The method of claim 7, wherein the one or more antigens is an HPV protein or peptide.

9. The method of claim 8, wherein the one or more antigens comprise one or more of the gp100 sequence (KVPRNQDWL [SEQ ID NO: 8]) and the TRP2 sequence (SYVDFFVWL [SEQ ID NO: 9]).

10. A method of augmenting an immune response in a mammal, said method comprising the step of administering an effective amount of a vaccine composition to the mammal, wherein the vaccine composition comprises an adjuvant and a therapeutic factor, wherein the adjuvant is a cationic lipid, and wherein the therapeutic factor is a cytokine selected from interleukins 1-18.

11. The method of claim 10, wherein the reduction results in an increase in T-cell response in the mammal.

12. The method of claim 11, wherein the T-cell response is a CD8+ T-cell response.

13. The method of claim 10, wherein the cationic lipid is selected from the group consisting of DOTAP, DOTMA, DOEPC, and combinations thereof.

14. The method of claim 13, wherein the cationic lipid is DOTAP.

15. The method of claim 14, wherein the adjuvant is an enantiomer of the cationic lipid.

16. The method of claim 15, wherein the enantiomer is R-DOTAP.

17. The method of claim 10, wherein the composition further comprises one or more antigens.

18. The method of claim 17, wherein the one or more antigens is an HPV protein or peptide and wherein the antigen comprises one or more of the gp100 sequence (KVPRNQDWL [SEQ ID NO: 8]) and the TRP2 sequence (SYVDFFVWL [SEQ ID NO: 9]).

* * * * *